United States Patent [19]

Wong

[11] Patent Number: 5,721,430

[45] Date of Patent: Feb. 24, 1998

[54] PASSIVE AND ACTIVE INFRARED ANALYSIS GAS SENSORS AND APPLICABLE MULTICHANNEL DETECTOR ASSEMBLES

[75] Inventor: Jacob Y. Wong, Santa Barbara, Calif.

[73] Assignee: Engelhard Sensor Technologies Inc., Iselin, N.J.

[21] Appl. No.: 583,993

[22] Filed: Jan. 11, 1996

Related U.S. Application Data

[63] Continuation-in-part of Ser. No. 422,507, Apr. 13, 1995.
[51] Int. Cl.⁶ .......................... G01N 21/35; G01N 21/61
[52] U.S. Cl. ........................ 250/339.13; 250/338.5; 250/343
[58] Field of Search ............... 250/343, 339.13, 250/339.01, 339.02, 338.5

[56] References Cited

U.S. PATENT DOCUMENTS

| | | | |
|---|---|---|---|
| 3,032,655 | 5/1962 | Romans | 250/43.5 |
| 3,662,171 | 5/1972 | Brengman et al. | 250/339.04 |
| 3,793,525 | 2/1974 | Burch et al. | 250/343 |
| 3,811,776 | 5/1974 | Blau, Jr. | 356/51 |
| 4,456,919 | 6/1984 | Tomita et al. | 357/28 A |
| 4,500,207 | 2/1985 | Maiden | 356/409 |
| 4,520,265 | 5/1985 | Griggs et al. | 250/338.5 |
| 4,527,896 | 7/1985 | Irani et al. | 356/43 |
| 4,578,762 | 3/1986 | Wong | 364/497 |
| 4,694,173 | 9/1987 | Wong | 250/343.5 |
| 4,709,150 | 11/1987 | Burough et al. | 250/338 |
| 4,722,612 | 2/1988 | Junkert et al. | 374/124 |
| 4,765,752 | 8/1988 | Beynon et al. | 374/127 |
| 4,772,790 | 9/1988 | Aldridge | 250/343 |

(List continued on next page.)

OTHER PUBLICATIONS

Brochure dated Jun. 16, 1993 regarding OAI MIR–100 Thermopile (2 pgs.).
Thermopile MIR–100 Line Catalog Book (6 pgs.).
ARMTEC Industries, Inc. brochure regarding Northwoods PS–20 dector (2 pgs.) (undated).
Action et al., *AIAA Journal*, vol. 11, No. 7 (Jul. 1973), pp. 899–900 (Article entitled "Remote Measurement of Carbon Monoxide by a Gas Filter Correlation Instrument").

Primary Examiner—Carolyn E. Fields
Attorney, Agent, or Firm—Lyon & Lyon LLP

[57] ABSTRACT

Multichannel infrared detector assemblies for use in the detection and monitoring of gas concentrations are provided. The detector assemblies include a detector housing having a port for receiving infrared radiation therethrough; a substrate mounted within the detector housing, the substrate having three apertures therein to transmit radiation entering the detector assembly therethrough; a first, a second and a third thermopile detector fabricated on the bottom side of the substrate, the hot junctions of each thermopile detector positioned over one of the apertures in the substrate so as to receive radiation transmitted through the aperture, and the cold junctions of each thermopile detector positioned over the substrate; a first interference bandpass filter mounted on the top side of the substrate so that the first filter covers the aperture above the first detector and the first filter is interposed between the port and the first detector, the first interference bandpass filter designed to pass incident radiation at a first spectral band; a second interference bandpass filter mounted on the top side of the substrate so that the second filter covers the aperture above the second detector and the second filter is interposed between the port and the second detector, the second interference bandpass filter designed to pass radiation at a second spectral band; and a third interference bandpass filter mounted on the top side of the substrate so that the third filter covers the aperture above the third detector and the third filter is interposed between the port and the third detector, the third interference bandpass filter designed to pass radiation at a third spectral band. The disclosed infrared detector assemblies can be used in traditional NDIR gas sensors having an active source or in passive infrared analysis gas sensors which use a passive infrared temperature source and the space between the detector assembly and the source as the sample chamber.

38 Claims, 14 Drawing Sheets

U.S. PATENT DOCUMENTS

| | | | |
|---|---|---|---|
| 4,790,324 | 12/1988 | O'Hara et al. | 128/664 |
| 4,980,847 | 12/1990 | Hirano | 364/557 |
| 5,026,992 | 6/1991 | Wong | 250/343 |
| 5,041,723 | 8/1991 | Ishida et al. | 250/339.13 |
| 5,060,508 | 10/1991 | Wong | 73/31.02 |
| 5,095,913 | 3/1992 | Yelderman et al. | 250/339.13 |
| 5,100,479 | 3/1992 | Wise et al. | 136/226 |
| 5,163,332 | 11/1992 | Wong | 73/863.23 |
| 5,165,796 | 11/1992 | Gat et al. | 250/339.04 |
| 5,186,541 | 2/1993 | Paulk | 374/124 |
| 5,222,389 | 6/1993 | Wong | 73/31.02 |
| 5,326,173 | 7/1994 | Evans et al. | 374/128 |
| 5,340,986 | 8/1994 | Wong | 250/343 |
| 5,444,249 | 8/1995 | Wong | 250/343 |

| PASSIVE SOURCE TEMP °C/°K | R3.91µ $\times 10^{-4}$ Wcm$^{-2}$µ$^{-1}$ | R4.67µ $\times 10^{-4}$ Wcm$^{-2}$µ$^{-1}$ | R5.00µ $\times 10^{-4}$ Wcm$^{-2}$µ$^{-1}$ | $\dfrac{R3.91}{R5.00}$ | $\dfrac{R5.00}{R3.91}$ |
|---|---|---|---|---|---|
| 5 / 278 | 0.7304 | 2.5907 | 3.8267 | 0.1909 | 5.2392 |
| 10 / 283 | 0.9229 | 3.1511 | 4.5946 | 0.2009 | 4.9784 |
| 15 / 288 | 1.1566 | 3.8067 | 5.4818 | 0.2110 | 4.7396 |
| 20 / 293 | 1.4384 | 4.5691 | 6.5009 | 0.2213 | 4.5195 |
| 22 / 295 | 1.5663 | 4.9067 | 6.9485 | 0.2254 | 4.4365 |
| 25 / 298 | 1.7758 | 5.4507 | 7.6655 | 0.2317 | 4.3166 |
| 30 / 303 | 2.1772 | 6.4647 | 8.9898 | 0.2422 | 4.1291 |
| 35 / 308 | 2.6517 | 7.6250 | 10.488 | 0.2528 | 3.9552 |
| 40 / 313 | 3.2092 | 8.9462 | 12.177 | 0.2636 | 3.7944 |
| 45 / 318 | 3.8608 | 10.444 | 14.071 | 0.2744 | 3.6446 |

*FIG. 3*

PASSIVE AND ACTIVE INFRARED ANALYSIS GAS SENSORS AND APPLICABLE MULTICHANNEL DETECTOR ASSEMBLES

This application is a continuation-in-part of co-pending application Ser. No. 08/422,507, filed Apr. 13, 1995. Application Ser. No. 08/422,507 is incorporated by reference as if fully set forth herein.

BACKGROUND OF THE INVENTION

1. Field of the Invention

The present invention generally relates to the field of gas sensing devices. More particularly, the present invention relates to gas detectors capable of measuring the concentrations of one or more gases using a characteristic infrared absorption band of the gas to be detected.

2. Description of the Prior Art

Many gases have characteristic absorption bands falling within the infrared spectrum. The nondispersive infrared (NDIR) technique has been widely used in the gas analyzer industry for the detection of these gases. Such gas analyzers utilize the principle that various gases exhibit substantial absorption at characteristic wavelengths in the infrared radiation spectrum. Typically, a narrow-band optical or infrared transmission filter is used to isolate the wavelength band of interest in NDIR gas analyzers. On the other hand, a prism or diffraction grating is used in gas analyzers relying on dispersive techniques.

The NDIR technique, which is generally classified as a non-interactive gas analysis technique, offers a number of advantages over previous interactive types of gas measurement methods including electrochemical fuel cell, sintered semiconductor (tin dioxide), catalytic (platinum bead) and thermal conductivity. These advantages include speed of response, gas detection specificity, long term measurement stability, reduced maintenance, and greater specificity. Moreover, in some cases the interactive gas sensor can be poisoned into a nonfunctional state. Depending on the application, this could place human life at risk.

Interactive gas sensors are generally nonspecific because the reagent being used to determine the concentration of the desired gas may react with other gases that are present. This will naturally result in false readings. Further, if the equilibrium of the reaction between the nonspecific gas and the reagent is such that the gas and reagent remain reacted even after the partial pressure of the gas drops in the environment being monitored, the sensor will no longer function properly and is poisoned.

The response time for NDIR gas sensors is typically shorter than that for interactive gas sensors because the kinetics of the reaction between the sample gas and reagent controls how quickly the reactive type sensor can detect a change in the concentration of the gas in the environment being monitored.

Despite the fact that interactive gas sensors are unreliable and that the NDIR gas measurement technique is one of the best, NDIR gas analyzers have not enjoyed wide spread application because of their complexity and high cost of implementation.

Over the years, a large number of measurement techniques based upon the NDIR principle for the detection of gases have been proposed and successfully demonstrated. In the past, NDIR gas analyzers typically included an infrared source, a motor-driven mechanical chopper to modulate the source, a pump to push or pull gas through a sample chamber, a narrow bandpass interference filter, a sensitive infrared detector plus expensive infrared optics and windows to focus the infrared energy from the source onto the detector.

The most notable of these types of analyzers are shown and described in U.S. Pat. No. 3,793,525 to Burch, et al., U.S. Pat. No. 3,811,776 to Blau, Jr., and U.S. Pat. No. 4,578,762 to Wong. These NDIR gas analyzers perform well functionally and have contributed greatly to the overall technical advancement in the field of gas analysis during the past two decades. However, their overall size, complexity, and cost have precluded their use in a number of applications.

The need for better and lower cost gas analyzers has led to newer inventions. For example, U.S. Pat. No. 4,500,207 to Maiden and U.S. Pat. Nos. 4,694,173 and 5,026,992 to Wong have proposed NDIR techniques for gas detection that do not use any moving parts such as mechanical choppers. The goal of these patents has been to produce NDIR gas sensors that are more rugged and compact, thus opening up a host of new applications.

In an attempt to further reduce the cost and simplify the implementation of the NDIR technique, a low-cost NDIR gas sensor technique was developed. The low-cost NDIR technique employs a diffusion-type gas sample chamber of the type disclosed in U.S. Pat. No. 5,163,332, issued in Nov. 17, 1992, to the present applicant, and hereby incorporated by reference. This diffusion-type gas sample chamber eliminates the need for: expensive optics, mechanical choppers, and a pump for pushing or pulling the gas into the sample chamber. As a result, a number of applications for the NDIR technique, which were previously considered impractical because of cost and complexity, have been opened.

A similar guiding principle led to the development of the improved NDIR gas sensor disclosed by Wong in U.S. Pat. No. 5,444,249, issued Aug. 22, 1995. This patent describes a simple, low-cost diffusion-type NDIR gas sensor which can be micromachined out of a semiconductor material such as Si or GaAs, thus allowing the entire sensor to be placed on a microchip.

Although the low-cost NDIR gas sensor technique of U.S. Pat. No. 5,163,332 and the improved NDIR gas sensor of U.S. Pat. No. 5,444,249 have opened a wide variety of new applications, these gas sensors still require too much power to be used in many potential gas sensor applications. As a result, applications in which low-cost, solid-state gas sensors may be used remain limited.

If a gas analysis technique could be developed which required no moving parts, had the same degree of specificity as the NDIR technique, was low cost, and had relatively low power demands so that devices employing the technique could be battery operated over an extended period of time, the applications in which gas sensors are used and the frequency of their use would increase dramatically. Therefore, while a long felt need exists for a simple, compact, inexpensive gas sensor that has low power requirements, this need has gone unfilled. Accordingly, a goal of the present invention is to further advance the technique of infrared gas analysis by providing a compact, reliable, low cost, and low power infrared gas sensor using infrared absorption. Another goal of the present invention is to provide infrared detector assemblies which can be used in the infrared gas sensors according to the present invention.

SUMMARY OF THE INVENTION

The present invention is directed toward an infrared gas sensor for detecting the concentration of one or more predetermined gases using a novel infrared gas analysis technique referred to as passive infrared analysis (PIA). The PIA technique of the present invention is simpler than the NDIR gas analysis techniques known to date in that it does not require an "active" infrared source, nor does it require a structurally defined sample chamber. As a result, small, solid-state, low-cost and low power gas sensors can be constructed to meet a host of special applications hitherto impossible using presently available NDIR gas analyzers.

The present invention recognizes that all objects greater than 0 kelvin emit radiation. The present invention takes advantage of this fact by using ordinary objects, such as walls, ceilings, floors, etc. as a "passive" source of infrared radiation. These "passive" infrared radiation sources can be effectively used in some cases to replace the "active" infrared radiation sources that have been used almost exclusively hitherto in all NDIR gas analyzers.

The "active" infrared source used in conventional NDIR gas sensors is typically a heated and very hot object (500°–1000° C.) such as nichrome wire imbedded in alumina ceramic (Nerst glower) or a resistive tungsten wire of a small incandescent light bulb. These sources are characterized as "active" sources because they are powered by the gas sensor. On the other hand, a "passive" source, as used herein, is any object that is above 0 kelvin, but which is not powered by the gas detector power supply. Typical passive infrared sources that will be used by the infrared gas sensor of the present invention include walls, carpets, tile floors, ceilings, and furnace walls to name just a few. Clearly, however, as those skilled in the art will recognize from the teachings of the present disclosure, the passive infrared sources which can be used by the gas sensor of the present invention are virtually unlimited. However, the temperature of the passive infrared source should be greater than the temperature of the gas to be measured. That is to say that the law of detailed balance must be observed.

Although the temperature of active infrared sources is very high, the source area is typically quite small. A source area on the order of a few $mm^2$ is not uncommon. On the other hand, although the temperature of typical indoor passive infrared source is only about 300K or –25° C., if the utilized source area is approximately 1000 times larger than that of conventional infrared sources, then using Planck's equation it can be shown that the spectral radiant emittance for the passive infrared source is comparable to that of conventional active sources in the spectral region from 3 to 20 microns. The passive infrared source area required for proper gas detection will depend on the temperature range expected from the passive infrared source.

In the PIA technique employed in the present invention, the passive infrared source must be characterized. To characterize the passive infrared source, a detector assembly is provided that is capable of measuring the spectral emittance from the selected passive infrared source at two different spectral bands. The spectral bands used for characterizing the source are preferably "neutral" spectral bands. Neutral spectral bands are spectral bands which are chosen so that they are not absorbed, or only moderately absorbed, by any of the gases that are typically found in the environment to be monitored.

Based on Planck's Law, the ratio of outputs measured at the two neutral spectral bands can be used to uniquely determine the temperature of the passive infrared source assuming the two neutral spectral bands are close enough so that the variation of the emissivity function for the source is insignificant.

To determine the concentration of the gas to be detected, the detector assembly also measures the amount of incident radiation at a "non-neutral" spectral band that coincides with an absorption band of the gas to be measured. This output, therefore, is indicative of the concentration of the gas within the angle subtended by the detector assembly to the passive infrared source. By using the output measured at at least one of the neutral spectral bands, the output measured at the non-neutral spectral band and the calculated temperature, the concentration of the gas within the angle subtended by the detector assembly to the passive infrared source can be determined.

According to one embodiment of the present invention, a passive source infrared gas detector which uses an ambient temperature source, higher in temperature than the surrounding gas, and the space between the detector assembly and the source as the sample chamber is provided. The gas detector comprises an infrared detector assembly for producing a first output, a second output, and a third output, the first output being indicative of the radiation received by the detector assembly at a first non-neutral spectral band which is absorbable by a preselected gas to be detected, the second output being indicative of the radiation received by the detector assembly at a first neutral spectral band from the passive infrared source, and the third output being indicative of the radiation received by the detector assembly at a second neutral spectral band from the passive infrared source. Signal processing means are included for manipulating the three outputs to determine the concentration of the gas being monitored. By adding additional detectors to the detector assembly that can detect radiation at spectral bands characteristic of additional gases, the infrared gas detector can be used to monitor the concentration of a plurality of gases.

According to another embodiment of the present invention, a passive source infrared gas detector is provided which comprises:

a. an infrared detector assembly comprising i. a port for receiving radiation therethrough from the passive infrared source, ii. a first sensor, a second sensor, and a third sensor disposed to receive radiation through the port for producing a first output, a second output, and a third output indicative of the radiation incident on the first sensor, second sensor, and third sensor, respectively, iii. a first narrow bandpass filter interposed between the port and the first sensor, the first narrow band bass filter producing an output therefrom indicative of the radiation incident on the first bandpass filter at a first non-neutral spectral band which is absorbable by a preselected gas to be detected, iv. a second narrow bandpass filter interposed between the port and the second sensor, the second narrow bandpass filter producing an output therefrom indicative of the radiation incident on the second bandpass filter at a first neutral spectral band, and v. a third narrow bandpass filter interposed between the port and the third sensor, the third narrow bandpass filter producing an output therefrom indicative of the radiation incident on the third bandpass filter at a second neutral spectral band, b. temperature measuring means for producing an output corresponding to the ambient temperature of the first, second, and third sensors;

c. signal processing means adapted to receive the outputs from the first sensor, second sensor, third sensor, and temperature measuring means and for sampling and at least temporarily storing the outputs of the first sensor, second sensor, third sensor, and temperature measuring means at preset intervals, the signal processing means including means for i. correcting the stored outputs of the first sensor, second sensor, and third sensor to compensate for the ambient temperature of the first sensor, second sensor, and third sensor, respectively, for the sampling period,
   ii. calculating the temperature of the passive infrared source for the sampling period based on the ratio of the corrected values of the outputs from the second and third sensors,
   iii. calculating a predicted output for at least one of the second or third sensors based on the calculated temperature of the passive infrared source for the sampling period,
   iv. calculating an attenuation factor by comparing the predicted output of at least one of the second or third sensors with the corrected output from the corresponding sensor for the sampling period,
   v. correcting the stored output of the first sensor by the attenuation factor,
   vi. determining the concentration of the gas for the sampling period from the corrected output from the first sensor, and
   vii. monitoring the concentration of gas based on a predetermined function and providing an output signal based on the monitoring.

Thus, the infrared gas sensor according to the present invention uses a passive infrared source in a novel PIA technique which effectively eliminates the need for a hot "active" infrared source that is used in conventional NDIR gas measurement devices. Furthermore, in the PIA technique employed in the infrared gas sensor of the present invention, the space between the passive infrared source, for example a certain portion of a wall, and the detector assembly becomes the sample chamber. In other words, the present invention not only eliminates the "active" infrared source, but it also eliminates the need for the sample chamber used in conventional NDIR gas analyzers.

Due to the fact that an "active" infrared source is not required for the implementation of the present invention, the power consumption of a infrared gas sensor according to the present invention can be significantly reduced, thus making the simple passive infrared gas sensor of the present invention battery operable for an extended period of time. Moreover, the size of the sensor can be reduced because a structurally defined gas chamber is no longer necessary.

Accordingly, it is an object of this invention to provide an apparatus and method for measuring the concentration of one or more gases using a novel infrared analysis technique referred to as passive infrared analysis (PIA). It is also an object of the present invention to provide an improved infrared detector assembly which can be used in the gas sensor according to the present invention.

To this end a passive source infrared detector assembly is provided, comprising: a detector housing having a port for receiving infrared radiation therethrough; a substrate mounted within the detector housing, the substrate having three apertures therein to transmit radiation entering the detector assembly therethrough; a first, a second and a third thermopile detector fabricated on the bottom side of the substrate, the hot junctions of each thermopile detector positioned over one of the apertures in the substrate so as to receive radiation transmitted through the aperture, and the cold junctions of each thermopile detector positioned over the substrate; a first interference bandpass filter mounted on the top side of the substrate so that the first filter covers the aperture above the first detector and the first filter is interposed between the port and the first detector, the first interference bandpass filter designed to pass incident radiation at a first non-neutral spectral band which is absorbable by a preselected gas to be monitored; a second interference bandpass filter mounted on the top side of the substrate so that the second filter covers the aperture above the second detector and the second filter is interposed between the port and the second detector, the second interference bandpass filter designed to pass radiation at a first neutral spectral band; a third interference bandpass filter mounted on the top side of the substrate so that the third filter covers the aperture above the third detector and the third filter is interposed between the port and the third detector, the third interference bandpass filter designed to pass radiation at a second neutral spectral band; and signal processing circuitry connected to the electrical outputs produced by the first, second, and third detectors for producing a signal in response thereto representative of the concentration of the gas being measured.

In another aspect of the present invention, it is an object to provide an infrared detector assembly which can be used in a NDIR gas sensor having an active source or in a PIA gas sensor of the present invention. To this end, an infrared detector assembly is provided comprising: a detector housing having a port for receiving infrared radiation therethrough; a substrate mounted within the detector housing, the substrate having three apertures therein to transmit radiation entering the detector assembly therethrough; a first, a second and a third thermopile detector fabricated on the bottom side of the substrate, the hot junctions of each thermopile detester positioned over one of the apertures in the substrate so as to receive radiation transmitted through the aperture, and the cold junctions of each thermopile detector positioned over the substrate; a first interference bandpass filter mounted on the top side of the substrate so that the first filter covers the aperture above the first detector and the first filter is interposed between the port and the first detector, the first interference bandpass filter designed to pass incident radiation at a first spectral band; a second interference bandpass filter mounted on the top side of the substrate so that the second filter covers the aperture above the second detector and the second filter is interposed between the port and the second detector, the second interference bandpass filter designed to pass radiation at a second spectral band; and a third interference bandpass filter mounted on the top side of the substrate so that the third filter covers the aperture above the third detector and the third filter is interposed between the port and the third detector, the third interference bandpass filter designed to pass radiation at a third spectral band. When the present sensor is to be used in a traditional NDIR application, an active infrared light source can be operatively mounted within the detector assembly. Further, the infrared detector assembly can be used in NDIR applications employing an active source to detect up to as many gases as there are thermopile/filter combinations in the infrared detector assembly by appropriately selecting the spectral bands passed by the respective bandpass filters to pass wavelengths at which the desired gases to be detected strongly absorb infrared radiation. If fewer gases need be detected than the number of thermopile/filter combinations, the unneeded detector channels can be disabled.

Further objects and advantages of the invention will be better understood from the following description considered in connection with accompanying drawings in which the preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 3 is a table depicting the value of the ratio of the spectral radiant emittances for 0.1 micron spectral bands having center wavelengths of 5.00 and 3.91 microns as a function of the temperature of the "passive" infrared source. The emissivity values for both spectral bands are assumed to be the same.

DETAILED DESCRIPTION OF THE INVENTION

Figure 1:
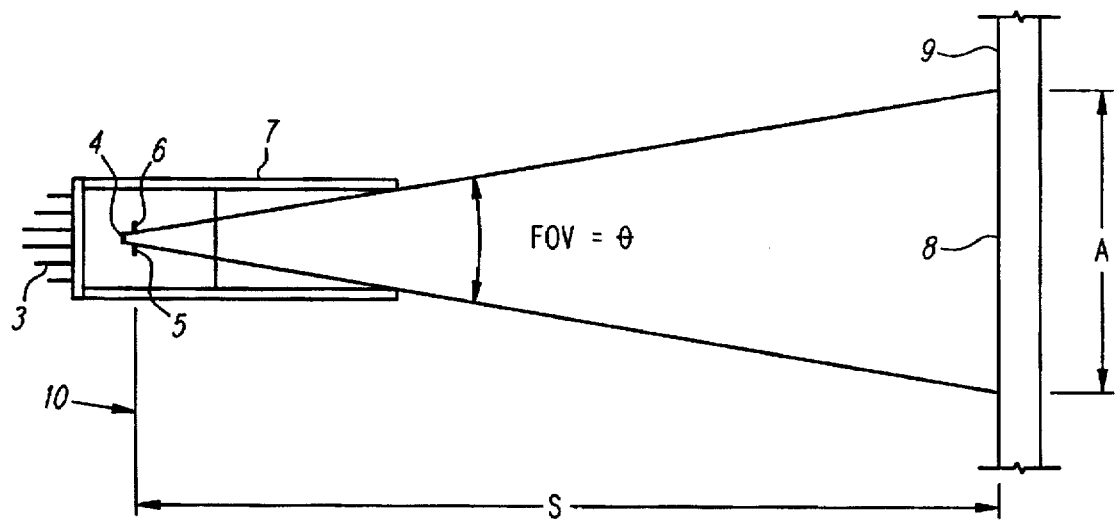
FIG. 1 shows a preferred embodiment of the present invention depicting the detector assembly, the passive infrared source (wall) and the intervening space between the passive infrared source and the detector assembly constituting the sample chamber.

A preferred embodiment of a PIA gas sensor according to the present invention is now described with reference to FIG. 1. FIG. 1 depicts a detector assembly 3 comprising one signal detector 4 equipped with a narrow bandpass interference filter $F_1$ (not shown) whose center wavelength (CWL) $L_1$ coincides with the absorption band of the gas to be measured. In addition, detector assembly 3 includes two source characterizing detectors 5 and 6 equipped respectively with narrow bandpass filters $F_2$ and $F_3$ (not shown) whose CWL's $L_2$ and $L_3$, do not coincide with any known gases or vapors commonly found in the atmosphere. In other words, at wavelengths $L_2$ and $L_3$, there should be no absorption bands (or at least extremely weak ones) for commonly encountered gases or vapors in the atmosphere being measured. For air, neutral wavelengths can be found at 3.91 µm, 5.00 µm, and 9.00 µm.

If carbon monoxide (CO) is the desired gas to be detected, then the CWL and the full width at half maximum (FWHM) values for the interference filter associated with detector 4 are chosen to be 4.67 µm and 0.1 µm, respectively. On the other hand, if $CO_2$ is the desired gas to be detected, the CWL and FWHM for the interference bandpass filter associated with detector 4 are set at 4.26 and 0.1 µm, respectively. As one skilled in the art would recognize, this technique has application to many other gases that have an absorption band in the infrared, including $H_2O$ and Total Volatile Organic Chemicals (TVOC's).

Typically, the CWL $L_1$ of the interference filter $F_1$ associated with detector 4 will be selected so that it falls as close as possible to the middle of the absorption band being used for the gas of interest. This will ensure that the maximum amount of radiation at the spectral band being monitored is absorbed by the gas, thus increasing the sensitivity and accuracy of the detector. However, in the case of gases which are very strong absorbers like $CO_2$, it may be necessary to shift the CWL $L_1$ of the interference filter $F_1$ for detector 4 to ode side of the absorption band so that not as much light is absorbed at the spectral band being monitored. Such a shift should be considered when very long pathlengths are being used or when the concentration of the gas is very high. This technique can be used to prevent the detector from becoming starved for light within the range of gas concentrations to be monitored.

The FWHM of interference filter $F_1$ associated with detector 4 is preferably selected so that it is about 0.1 µm so that the detector has a high degree of specificity. As those skilled in the art will recognize, however, other band widths may be selected depending on the width of the absorption band of the gas being monitored and the degree of specificity desired for the detector.

The CWL's $L_2$ and $L_3$ of the neutral spectral bands chosen for interference filters $F_2$ and $F_3$ should be selected as close in spectral position as possible to $L_1$. Although it is not necessary, it is also desirable for $L_1$ to fall between $L_2$ and $L_3$. For example, if CO or $CO_2$ are to be detected, $L_2$ and $L_3$ can be chosen to be 3.91 µm and 5.00 µm; respectively. Alternatively, $L_2$ and $L_3$ can be chosen to be 3.91 µm and 9.00 µm. In the present embodiment, the FWHM of $F_2$ and $F_3$ is preferably set at about 0.1 µm. The width of the spectral band passed by $F_2$ and $F_3$ should be narrow enough that it does not overlap with an absorption line of a gas that would be found in the atmosphere. By setting the CWL's of $L_2$ and $L_3$ equal to 3.91 and 5.00, respectively, and the FWHM of these detectors at 0.1 μm, no significant overlap should occur. Consequently, the outputs for detectors 5 and 6 are not affected by the concentration of the gas to-be-measured or any other commonly encountered gases or vapors in the atmosphere.

Detectors 4, 5, and 6 are all preferably thermopile detectors. However, as those skilled in the art would recognize, other infrared detectors may be used in the present invention, including Platinum Silicide Schottky photodiodes.

The field of view (FOV) of the detector assembly 3 is determined by the aperture collar 7 attached to the detector assembly as shown in FIG. 1. The detector assembly 3 subtends an area 8 (corresponding to area A) of the wall 9 which is used as the passive infrared source for the present invention. The effective sample path length S of the present infrared gas sensor is defined by the distance between the detector plane 10 of the detector assembly 3 and the wall 9.

The relation between the area A of the passive infrared source 8, and the solid angle subtended at it by the detector assembly 3, or OM, uniquely defines the sample path length S for the presently disclosed infrared gas sensor as follows:

Sample Path length S=[A/OM]*

Since the solid angle OM is a function of the FOV subtended by the detector assembly at the wall and can be adjusted at will by design, the sample path length S for the present invention is, therefore, an extremely useful variable. In other words, the low concentration detection of a gas with an extremely weak absorption band can be accommodated by making the path length S very long (several meters) in order to attain adequate modulation for such a detection. Indeed, as one skilled in the art will recognize, the path length S should be set depending on the amount of modulation desired. For example, when a very strong absorber such as $CO_2$ is being monitored, shorter path lengths should be considered. However, if the desired application calls for detection of gas concentrations in the ppb range, then longer path lengths may be called for.

Although virtually any path length can be selected, path lengths between 5 inches and 10 feet will typically be adequate, with most path lengths being between about 5 inches and 6 feet.

The output $V_1$ of the signal detector 4 is used to determine the concentration of the gas to be measured. The output $V_1$ of detector 4 depends upon a number of factors. First and foremost, it is a function of the temperature T and the emissivity ε of the passive infrared source 8 as governed by the spectral radiant emittance formula depicted in Equation [1] below. Furthermore, $V_1$ also depends upon system optical throughput, or attenuation, expressed as G (see Equation [1] below) and the concentration of the to-be-measured gas found between the detector assembly 3 and the passive infrared source 8. The concentration of the gas to-be-measured determines the value of the modulation factor M as shown in Equation [1] below.

Detectors 5 and 6, which are equipped with neutral filters $F_2$ and $F_3$, are used to dynamically characterize the passive infrared source 8 and the environment in real time for the signal channel monitored by detector 4. The ratio Z of the outputs of detectors 5 and 6 uniquely determines the temperature of source 8. Furthermore, once the temperature T of the source 8 is determined, the instantaneous values for the source emissivity ε, system optical throughput (or attenuation) G can also be quickly determined using Equation [1] below and comparing the actual outputs with stored values of the respective outputs at the temperature $T_0$ and emissivity $ε_0$ of a reference black body source measured while the system was initialized. The values for T, ε and G are continually updated in real time for the output of signal detector 4, enabling the latter to establish the concentration of the gas to be measured.

The presently disclosed simple infrared gas sensor is also capable of rejecting the influence of stray radiation by virtue of the fact that the passive infrared source 8 is generally never a good reflector. Hence the amount of stray radiation that can find its way into the FOV of the optical system is minimal. Furthermore, unless the stray radiation happens to be in the spectral band defined by the filters of the detector assembly, namely $L_2$ and $L_3$, they will be rejected. Even if they have energy within the spectral pass band of the sensor optical system, the emissivity is likely to be rather smooth and constant. In such a case, the neutral detectors will simply treat such stray radiation as an increase in the passive infrared source temperature 8 with the correct information related to the signal detector for proper processing.

The manner in which the concentration of the gas to-be-measured is determined from the outputs $V_1$, $V_2$, and $V_3$ of detectors 4, 5, and 6, respectively, is now described in connection with FIGS. 2 and 3.

Figure 2:
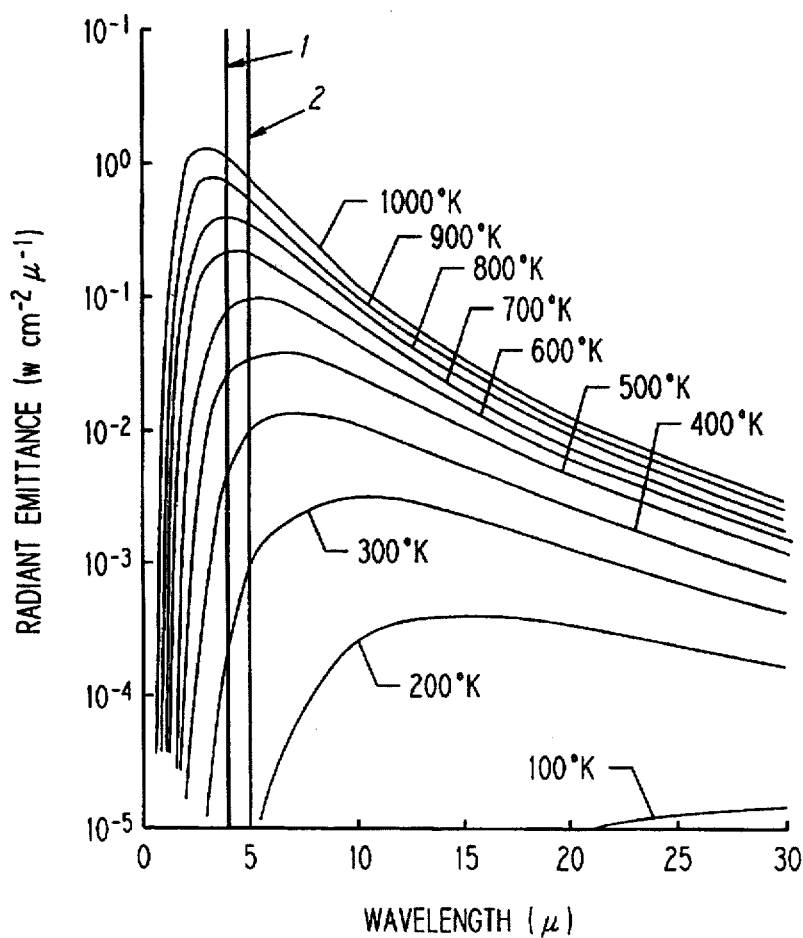
FIG. 2 is a graph showing the spectral radiant emittance of a black body at temperatures 100°–1,000° K.

FIG. 2 shows the spectral radiant emittance of a black body source at temperatures ranging from 100K to 1,000K. Several characteristics of the radiation from a black body source can be derived from these curves. First, the total radiant emittance which is proportional to the area under the curves, increases rapidly with temperature. The area under the curves being defined by the Stefan-Boltzmann equation and is thus proportional to the Stefan-Boltzmann constant times the absolute temperature to the fourth power. Second, the wavelength of maximum spectral radiant emittance shifts towards shorter wavelength as the temperature increases. This is referred to as Wien's displacement law, which is discussed more fully below. Third, the individual black body curves never cross one another; hence the higher the temperature, the higher the spectral radiant emittance at all wavelengths.

In conventional NDIR measurement systems using a black body, the infrared source is normally maintained at a constant and relatively high temperature (750–1,000K), and thus its spectral radiant emittance is typically represented by one of the curves above 700K in FIG. 2 dependent upon its absolute temperature. In contrast, the present invention relies on infrared radiation from passive infrared sources. As a result, the black body curves around 300K will typically reflect the radiant emittance of the typical sources used with the present invention. Such is the case with the wall 9 in FIG. 1.

The two narrow spectral bands 1 and 2 illustrated in FIG. 2 are centered at 3.91 μm and at 5.00 μm, which, as discussed above, are desirable wavelength bands for neutral detectors 5 and 6 when monitoring CO or $CO_2$. Because the bands illustrated in FIG. 2 correspond to the neutral spectral bands allowed to pass filters $F_2$ and $F_3$, they would preferably have a FWHM of 0.1 μm.

As seen from FIG. 2, the ratio (Z) of the spectral radiant emittances at these two wavelength bands uniquely determines the black body temperature. The only assumption made in this assertion is that the emissivity of the "passive" infrared source is approximately the same within the spectral band bounded by 3.91 μm and 5.00 μm. For almost all indoor walls which are either painted, wall-papered or wood-paneled, this is a good assumption.

Before determining the concentration of the gas being monitored, the passive source 8 must be characterized. The manner whereby the detectors 5 and 6 dynamically characterize the temperature and the emissivity of the passive infrared source 8 for the signal channel 4 is described as follows. For purposes of this discussion, detectors 4, 5, and 6 will be referenced as detectors $D_1$, $D_2$, and $D_3$.

Assuming that all three detector outputs $V_1$, $V_2$ and $V_3$ are initially referenced (i.e., initialized) to have values $V_{10}$, $V_{20}$ and $V_{30}$, respectively, at a known "passive" infrared source having temperature $T_o$, $\epsilon_o$, and area $A_o = OM \times S^2$, where OM is the solid angle corresponding to the FOV of the detector assembly 3 subtended by the passive source at the detector assembly, and S is the defined sample path length, one can write:

$$V_{i0} = R(T_o, \epsilon_o, L_i) A_o W_i r_i (a_i/(2\pi S^2)) GM \text{ volts} \quad \text{Equation [1]}$$

where i=1, 2 or 3;

$R(T_o, \epsilon_o, L_i)$ = The Spectral Radiant Emittance of the passive infrared source (Watt cm$^{-1}$ μ$^{-1}$), which is defined as $\epsilon_o(\lambda)$ multiplied by the spectral radiant emittance of a black body as defined by *Planck's Law* as $$(2\pi hc^2 \lambda^{-5})/(\exp(ch/k_B \lambda T) - 1);$$

$A_o$ = Area of passive infrared source;
$W_i$ = FWHM of $F_i$;
$r_i$ = Responsivity of detector $D_i$ (Volts/Watt);
$a_i$ = Area of detector $D_i$;
S = Sample path length;
G = System Optical Throughput (100%=unity);
and
M = Modulation by the gas to be measured.

When the detector assembly 3 faces a real time passive infrared source 8 of the area A (A is the same as the reference condition $A_0$ because OM and S are fixed by design in the embodiment illustrated in FIG. 1), temperature T and emissivity $\epsilon$, the outputs of $D_1$ are given by Equation [1] above as follows:

$$V_i = R(T, \epsilon, L_i) A W_i r_i (a_i/(2\pi S^2)) GM \text{ volts}$$

where i=1.

For the neutral channels $D_2$ (i=2) and $D_3$ (i=3). If we assume that $W_2 = W_3$; $r_1 = r_2$ (similar detectors); $a_2 = a_3$ (same detector areas); $G_2 = G_2$ (both detectors share the common optical system) and M=1.0 (neutral spectral bands for both $D_2$ and $D_3$), then the outputs of the detectors $D_2$ and $D_3$, namely $V_2$ and $V_3$, are the functions only of their respective spectral position $L_2$ and $L_3$, the temperature T and the emissivity $\epsilon$ of the passive infrared source 8. If we further assume that the emissivity $\epsilon$ of the passive infrared source 8 is the same for the narrow spectral region bounded by $L_2$ and $L_3$ (about one micron), then the ratio of the outputs $Z = V_2/V_3$ is only a function of temperature T of the passive infrared source 8, and the spectral positions $L_2$ and $L_3$.

As a matter of fact, the Planckian black body radiation physics together with the Wien's displacement law stipulate that the ratio of the spectral radiant emittances at two spectral positions, when appropriately spaced, uniquely determines the temperature of a particular black body source in certain parts of the Planckian black body domain. The present invention takes advantage of this fact and recognizes that in the spectral regions between 3–15 microns and black body temperatures between 250–350K, such a ratio can indeed uniquely determine the temperature of the black body. Furthermore, once the temperature T from the reference temperature $T_0$ is determined, the present value $V_2$ or $V_3$ of the respective neutral detector outputs can be used to deduce by calculations the changes (if any) for the other parameters, grouped together as a product, in Equation [1] above, namely the change in emissivity $\epsilon$ of the passive infrared source 8 from $\epsilon_0$, the change in the system optical throughput G and the change in the detector responsivity due to aging of the detector itself.

Thus by adding two detectors with neutral spectral bands to the detector assembly of the present invention, the ratio of the outputs Z of these two detectors can be used to characterize in real time the temperature of the passive infrared source 8. It is important to point out that since the changes in the other parameters in Equation [1] above, namely $\epsilon$, G and r are substantially the same for the two neutral detector channels, the value of the ratio Z, which is the only parameter needed to determine uniquely the temperature of passive infrared source 8, can always be obtained firsthand. After this vital information is attained, the individual preset values of the signal and neutral detector outputs ($V_{10}$, $V_{20}$, $V_{30}$, $T_0$, and $\epsilon_0$) can be used to further assess, via calculations, any changes in the other parameters in Equation [1]. Since the parameters needed to determine the concentration of the gas to-be-measured from the signal channel detector output in Equation [1] are T, $\epsilon$, G, r and M, and since the first four parameters are dynamically characterized by the two neutral detector channels for the signal detector channel, the present invention, as illustrated in the present embodiment, is capable of accurately measuring the concentration of gas without the need for an active infrared source and the accompanying gas sample chamber. The only proviso to this statement being that the passive infrared source needs to be at a temperature greater than the gas being monitored. When the passive infrared source and gas being monitored are in equilibrium, no absorption will be observed because the law of detailed balance requires the gas to emit the same amount of photons as it absorbs.

FIG. 3 illustrates how the ratio of the spectral radiant emittances at 3.91 μm and 5.00 μm varies as a function of the passive infrared source temperature from 5° C. (278K) to 45° C. (318K). For purposes of FIG. 3, the emissivity $\epsilon$ is assumed to be 1 at both 3.91 μm and 5.00 μm. In the vicinity of the 300K black body curves, the curves themselves are smooth and there is a very respectable difference in the value of the ratio as a function of the black body temperatures.

EXAMPLE 1

An example of how the concentration of the gas to-be-measured would be calculated from the outputs of $V_1$, $V_2$, and $V_3$ from detectors 4, 5, and 6 under a given set of circumstances using Equation [1] is now provided. With reference to Equation 1, the reference conditions for this example are defined as follows:

$T_0 = 298°$ K or 25° C.
$\epsilon_0 = 1.000$
$A_0$ = constant throughout example calculation
$W_i = 0.1$ micron for i=1 (Signal), 2 (neutral) and 3 (neutral)

$r_i$=Responsivity of Detector $D_i$, which is the same for i=1, 2 and 3

$a_i$=Area of Detector $D_i$, which is the same for i=1, 2 and 3 and remains constant $S=S_0$=constant throughout this example calculation $G_0$=System Throughput during initialization=1.0

M=modulation factor due to presence of gas to be measured=1.00 for detectors $D_2$ and $D_3$ If a constant C is defined as $C=a_i/(2\pi S^2)$, the constant is the same for each detector channel and remains unchanged throughout the calculation in the present example, because $a_i$ is the same for each detector and the sample path length is set by design. At the above reference conditions, and assuming that the signal detector $D_1$ has a CWL of 4.67 μm corresponding to the absorption band of carbon monoxide, the neutral detector $D_2$ has a CWL of 3.91 μm and the neutral detector $D_3$ has a CWL of 5.00 μm, the measured voltage outputs from Detectors $D_1$, $D_2$ and $D_3$ at initialization are as follows using Equation [1] and the table given in FIG. 3:

Output of detector $D_1$ (Signal at 4.67 μm)
$V_{10}=5.4507\times10^{-5} A_0 r_i C G_0 M$ volts
$=5.4507\times10^{-5}$ YM (where $Y=A_0 r_i C$)

Output of detector $D_2$ (Reference at 3.91 μm)
$V_{20}=1.7758\times10^{-5} Y G_0 M$ volts
$=1.7758\times10^{-5}$ Y volts Output of detector $D_3$ (Reference at 5.00 μm)
$V_{30}=7.6655\times10^{-5} Y G_0 M$ volts
$=7.6655\times10^{-5}$ Y volts The gas sensor is initialized by measuring the voltage outputs of each detector when no carbon monoxide is present and then when a known concentration of carbon monoxide gas is present within the field of view of the detector assembly. In this manner, a calibration curve for the gas sensor can be obtained as one skilled in the art would recognize. Following initiation, the sensor is ready to make real time measurements. For the present example, assume the following situation is encountered. The temperature of the passive infrared source has increased to 308° K or 35° C. and the emissivity ε of the passive infrared source 8 is 0.8. The optical attenuation factor G is new 0.9; in other words there is now a 10% attenuation of the signal from the passive infrared source 8. Also assume that the concentration of the carbon monoxide gas present within the field of view of the gas sensor causes a 2% modulation in the signal detected by the signal detector $D_1$. As a result, the modulation factor M decreases from 1.00 to 0.98 for the signal detector. There should be no modulation of the signal to the neutral channel detectors $D_2$, $D_3$ due to the carbon monoxide gas because the interference filters for the neutral channel detectors have been appropriately selected to avoid the absorption bands of carbon monoxide and other gases which may be found in the environment being monitored.

Under the conditions outlined above, the output voltages for the three detectors would be:

Output of detector $D_1$ (Signal at 4.67 microns)

$$V_1 = 7.6250 \times 10^{-5}(0.8) YGM$$
$$= 6.1000 \times 10^{-5} Y (0.9)(0.98) \text{volts}$$
$$= 5.3802 \times 10^{-5} Y \text{ volts.}$$

Output of detector $D_2$ (Reference at 3.91 microns)

$$V_2 = 2.6517 \times 10^{-5}(0.8) YGM$$
$$= 2.1214 \times 10^{-5} Y (0.9)(1.0) \text{volts}$$
$$= 1.90922 \times 10^{-5} Y \text{ volts.}$$

Output of detector $D_3$ (Reference at 5.00 microns)

$$V_3 = 10.488 \times 10^{-5}(0.8) YGM$$
$$= 8.3904 \times 10^{-5} Y (0.9)(1.0) \text{volts}$$
$$= 7.55136 \times 10^{-5} Y \text{ volts.}$$

As with the initialization voltage outputs, the table in FIG. 3 was used to obtain the spectral radiant emittances for each of the wavelengths being monitored.

The first step in determining the concentration of the carbon monoxide gas, or other gas to-be-measured, is to calculate the ratio Z of the outputs from the two reference detectors:

$$Z = \text{Voltage}(5.00)/\text{Voltage}(3.91)$$
$$= 7.55136/1.90922$$
$$= 3.9552$$

Using the table in FIG. 3, the temperature of the passive infrared source 8 is determined to be 35° C. As stated above, it has been assumed that the area of the passive infrared source 8 and the optical arrangement remain unchanged during the example.

If only the temperature needs correction, then the new voltage output for the neutral channel detector $D_2$ should be the initiation value of $1.7758\times10^{-5}$ Y volts multiplied by the ratio (2.6517/1.7758), which equals $2.6517\times10^{-5}$ Y volts. Since the two voltages are not the same, it is known that the emissivity ε or attenuation G or both are different than the initialization conditions. From the measured output of detector $D_2$ (3.91 microns) and what the initiation value for this neutral channel should be at 35° C., the product εG can be calculated as follows:

$$\varepsilon G = (1.90922 \times 10^{-5} Y \text{ volts})/(2.6517 \times 10^{-5} Y \text{ volts})$$
$$= 0.72$$

It should be noted that if the product of the emissivity $\varepsilon_0$ and attenuation $G_0$ during initialization is less than 1.0, then the initialization value would need to be normalized to what it would be for an emissivity $\varepsilon_0$ of 1.0 and an attenuation $G_0$ of 1.0. In this way, the ratio of the two voltage outputs will result in the product of the instantaneous value of the εG factor.

The same information can also be deduced from using the output voltage from the other neutral detector monitoring the 5.00 μm channel.

Once it is known that the temperature of the passive infrared source is 35° C. and the product of εG is 0.72, a corrected output voltage at the 4.67 μm, or signal, channel can be calculated from the measured output of detector $D_1$ as follows:

$5.3802\times10^{-5}$ Y volts $(5.4507/7.6250)\times(1/0.72) = 5.3417\times10^{-5}$ Y volts As can be observed from the calculation, the output voltage is corrected for the εG factor and for temperature. As a result, the ratio of this corrected voltage output and the initiation voltage output gives the modulation factor M as follows:

$$5.3417 \times 10^{-5} \, Y/5.4507 \times 10^{-5} \, Y=0.98.$$

Thus the above methodology correctly predicts the modulation factor for the signal detector $D_1$, which is monitoring the 4.67 micron channel.

To recap, the first step of the procedure is to obtain the temperature of the new passive infrared source 8 by calculating the ratio of the two reference detectors. The second step is to compare the measured value for either of the two neutral channels with its initiation value and deduce the "$\epsilon G$" factor. Both of these pieces of information are then used to correct for the measured output from the signal detector $D_1$ at 4.67 microns. The ratio of this corrected value and stored initiation value for the signal detector $D_1$ will then yield the modulation factor. The modulation factor is used to give the concentrations of the gas present by using a calibration curve, which can be stored in the signal processing circuitry as is known in the art.

It is important to point out that although the FWHM (i.e. $W_i$) of the neutral detectors were described above in connection with FIGS. 1–3 as being the same, it is unnecessary that the PIA detector of the present invention be designed to have equal neutral band widths. This is because $W_i$ for each neutral detector (as well as the signal detector) will always be a known parameter fixed during the fabrication of a particular PIA detector. Further, regardless of the FWHM value of each of the neutral detectors, the ratio Z of the radiant emittance detected at the two neutral wavelength bands will still uniquely define the temperature of the passive infrared source 8. This is because, as illustrated in Equation 1 above, the radiant emittance of the passive infrared source is a function of the area under the black body curves defined by Planck's Law multiplied by the emissivity $\epsilon$ of the source, which will typically be the same for each of the neutral channels.

The PIA gas sensor described in connection with FIGS. 1–3, therefore, can alternatively be designed so that the FWHM of $W_2$ and $W_3$ of $F_2$ and $F_3$ (i.e., the neutral channels) are set so that their corresponding detectors measure the spectral radiant emittance from the passive infrared source 8 over a several micron band rather than the 0.1 µm band suggested above. The spectral bands passed by each of the neutral interference filters can also overlap one another in such a system. The only limitations on such a configuration is that the two neutral detectors cannot measure the spectral radiant emittance for identical spectral bands and the emissivity $\epsilon$ of the passive infrared source should be relatively constant over each of the spectral bands. The two neutral detectors cannot measure the spectral radiant emittance for identical spectral bands because the ratio Z would always be one in such situations. The emissivity $\epsilon$ of the passive infrared source should be relatively constant to ensure that this factor cancels out when calculating the ratio Z, thus enabling the temperature T of the passive infrared source to be determined directly from the ratio of the outputs from the two neutral channels.

In the wavelength range of 8 µm to 14 µm, there is very little absorption by water and $CO_2$. As an example, therefore, the FWHM $W_2$ of interference filter $F_2$ can be set to pass light between 8 and 14 µm so that the detector 5 will measure the total amount of energy emitted by the passive source over this spectral band. If the spectral band passed by interference filter $F_3$ is narrower than that passed by $F_2$ then the ratio of the amount of energy detected by detectors 5 and 6 can still be used to uniquely determine the temperature of the passive infrared source 8 in real time as described above. Bandpass filter $F_3$ preferably passes a spectral band of light that is approximately half the width that bandpass filter $F_2$ passes; thus, $F_3$ could be designed to pass the spectral radiant emittance from the passive infrared source falling within the range of 9.5 µm and 12.5 µm. By setting the FWHM $W_3$ of interference filter $F_3$ at about one half the width of $W_2$ of interference filter $F_2$, good variability in the ratio Z as a function of the temperature of the passive infrared source 8 is ensured.

The advantage of designing the neutral channels in this manner is that significantly more energy will be detected by detectors 5 and 6, respectively. This improves the signal to noise ratio for the detector, thereby permitting a more accurate characterization of the passive infrared source.

As would be readily apparent to those skilled in the art from the foregoing, the infrared gas detector according to FIG. 1 can be used to monitor the concentration of a plurality of gases simply by adding additional detectors $D_i$ to the detector assembly 3 and appropriately selecting the CWL of interference filter $F_i$ to correspond to the characteristic absorption band of the gas desired to be monitored.

Figure 4:
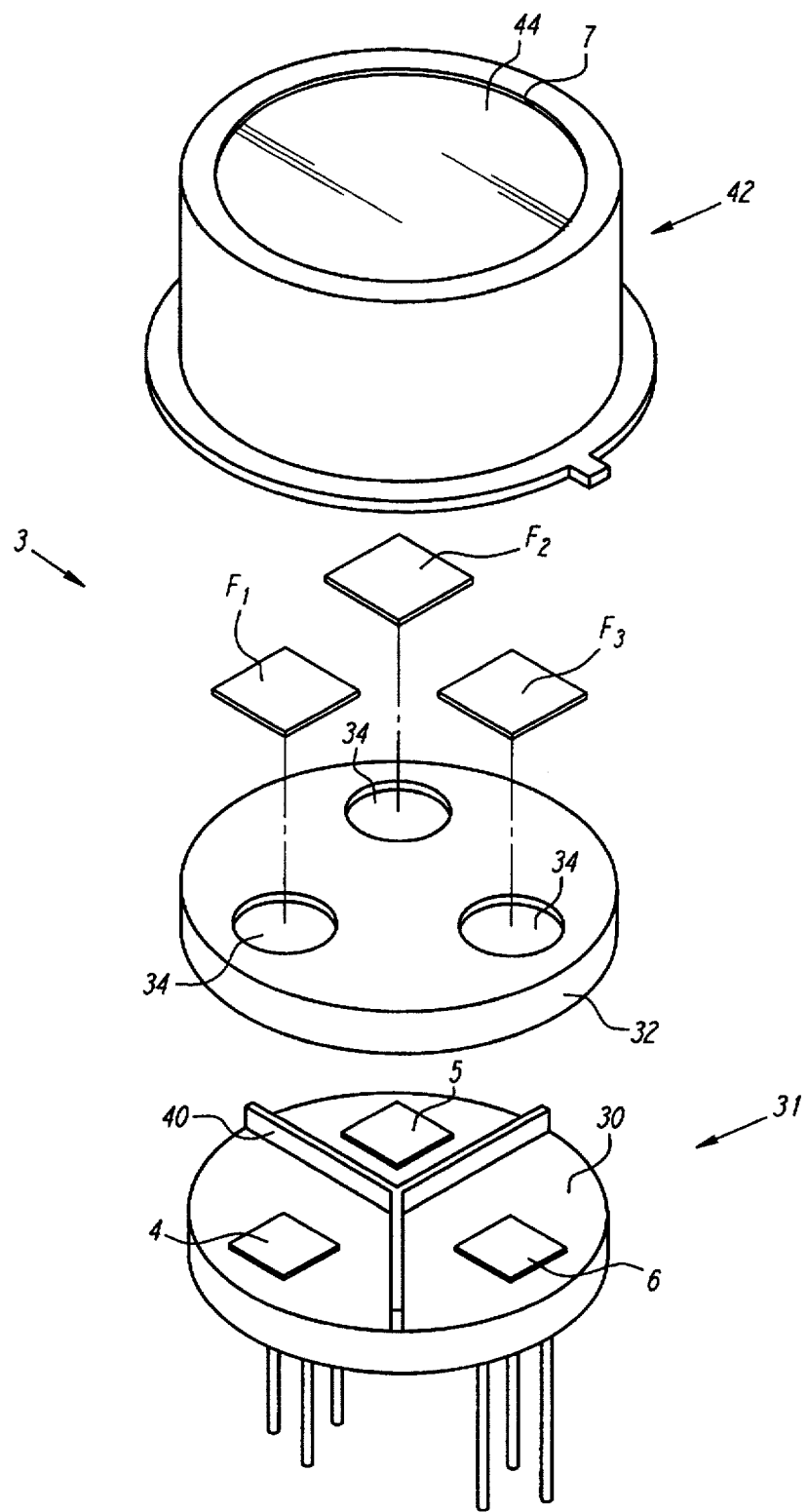
FIG. 4 is an exploded view of a detector assembly according to an embodiment of the present invention.
Figure 5:
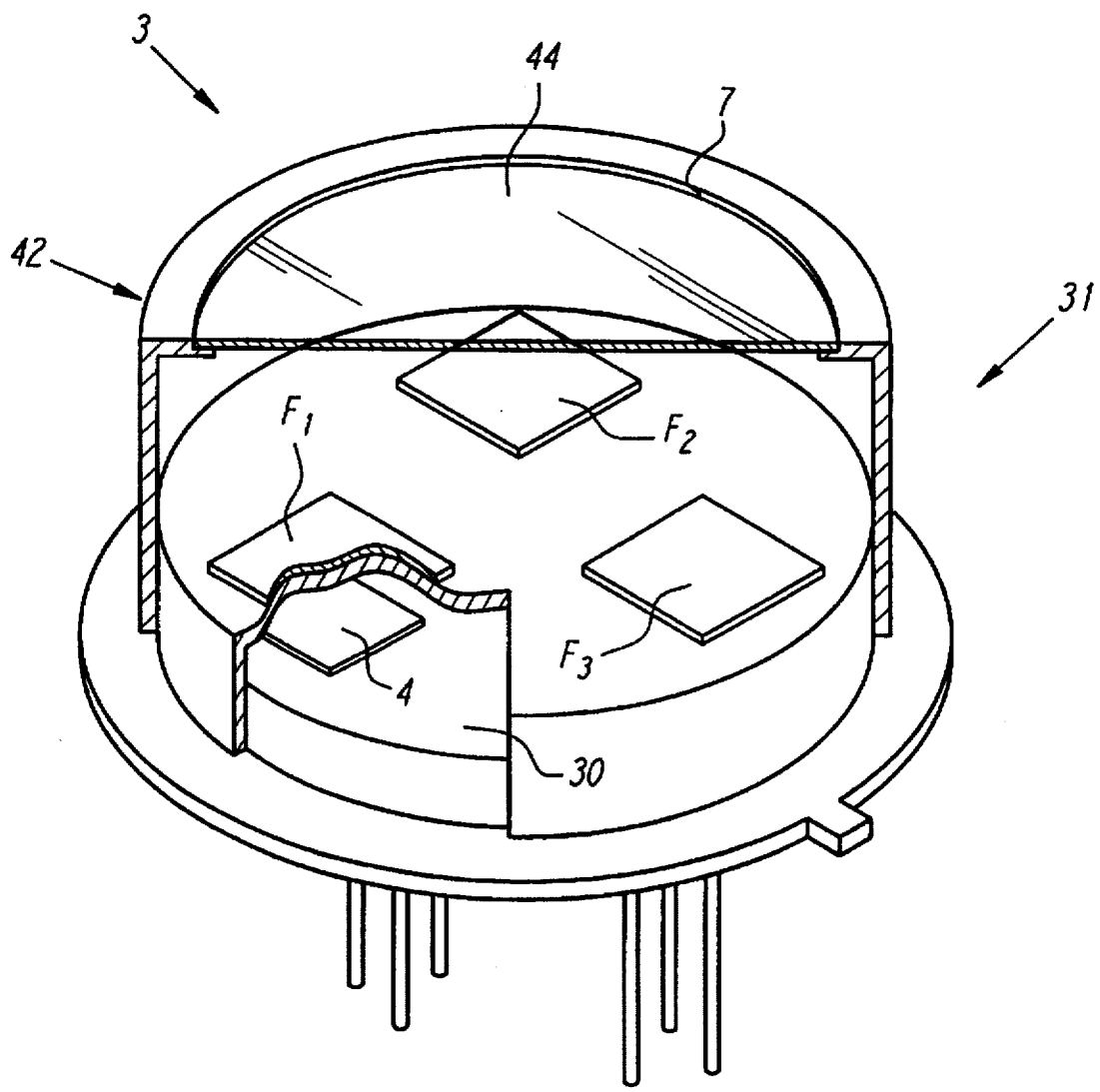
FIG. 5 is an oblique view showing a partial cutaway of the detector assembly illustrated in FIG. 4.

The construction of a detector assembly 3 according to one embodiment of the present invention is illustrated in FIGS. 4 and 5. As illustrated, the detector assembly is produced on a detector housing 31 such as a TO-5 can. The infrared detectors 4, 5 and 6 are mounted on a housing base 30 of the TO-5 can 31. Infrared detectors 4, 5 and 6 are in close proximity to one another so that the field of view of each detector overlaps substantially with one another.

While a variety of infrared detectors can be used in the present invention, detectors 4, 5 and 6 are preferably thermopiles due to the fact that thermopiles do not require any power, have a linear output, and have a very good signal to noise ratio. Although not required, it is also preferable to tie the reference junctions of each of the three detectors to the same thermal heat sink.

Filter mount 32 is disposed on top of housing base 30 so that the only radiation which can enter the space between the filter mount 32 and housing base 30 is the radiation that enters through the three apertures 34 located in filter mount 32. Apertures 34 are located in filter mount 32 so that each aperture is in axial alignment with one of the detectors.

Interference bandpass filters $F_1$, $F_2$ and $F_3$ cover apertures 34 so that they are interposed between the respective detector and the passive infrared light source. Furthermore, by covering the three apertures 34 located in filter mount 32 with interference filters $F_1$, $F_2$ and $F_3$, it is ensured that the only radiation that can enter the space between the filter mount 32 and the housing base 30 is that of the desired spectral bands. Divider 40 is used to prevent light of one spectral band from coming in contact with an infrared detector intended to measure light from a different spectral band.

The CWL and FWHM of bandpass filters $F_1$, $F_2$ and $F_3$ are set as described in connection with FIGS. 1–3.

The lid 42 to TO-5 can 31 acts as aperture collar 7 and thus defines the FOV for the detector assembly 3. The top of lid 42 comprises a light transmissive window 44. In selecting the material for window 44, it is preferable to select a material that is as transmissive as possible to the spectral bands being monitored by the detector assembly 3. Preferably, window 44 is equally transmissive for each of the spectral bands being monitored. Window materials which have relatively uniform transmission qualities over the range of 1 μm to 10 μm include silicon, $CaF_2$, and $BaF_2$. $CaF_2$ and $BaF_2$ are particularly preferred materials because of their high transmissivity in this range.

To save costs, window 44 may be eliminated altogether. However, by including window 44, the detector assembly 3 illustrated in FIGS. 4 and 5 can be hermetically sealed and thus increase the life expectancy for the detector assembly. Further, as dust and grease build up on the detector assembly 3, the output signal corresponding to the spectral bands will begin to drop. If the attenuation of the signal becomes too large, the infrared gas detector will not function properly. However, by including window 44 in detector assembly 3, the original signal strength can be easily restored by cleaning window 44. This is not possible if window 44 is omitted.

If a larger platform is desired so that additional detectors and bandpass filters can be added to enhance the capabilities of the infrared gas detector of the present embodiment, a TO-8 or larger package can be selected. For instance, such a platform might be used if the ability to monitor a plurality of gases is desired.

Figure 9:
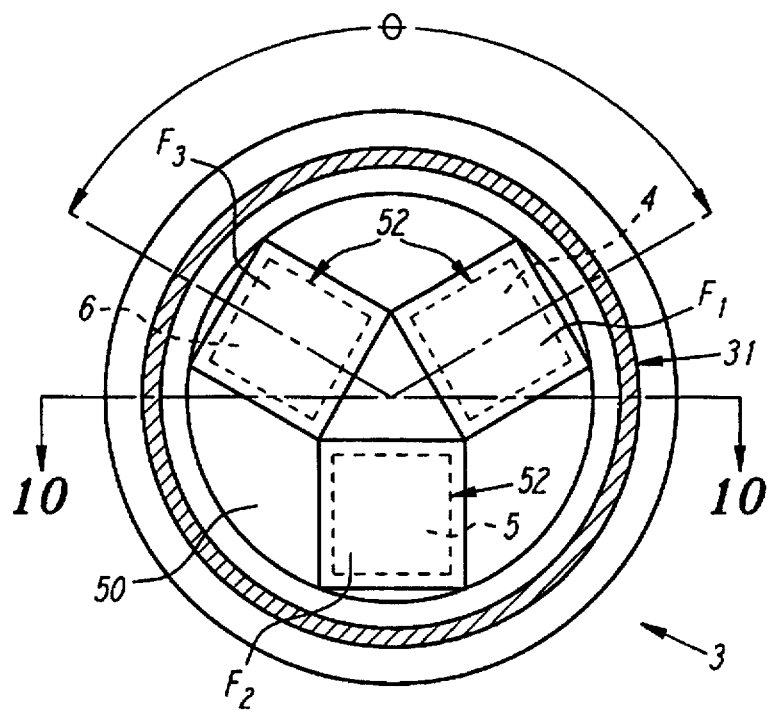
FIG. 9 is a transverse cross sectional view taken along line 9—9 of FIG. 10 of another embodiment of a detector assembly according to the present invention.
Figure 10:
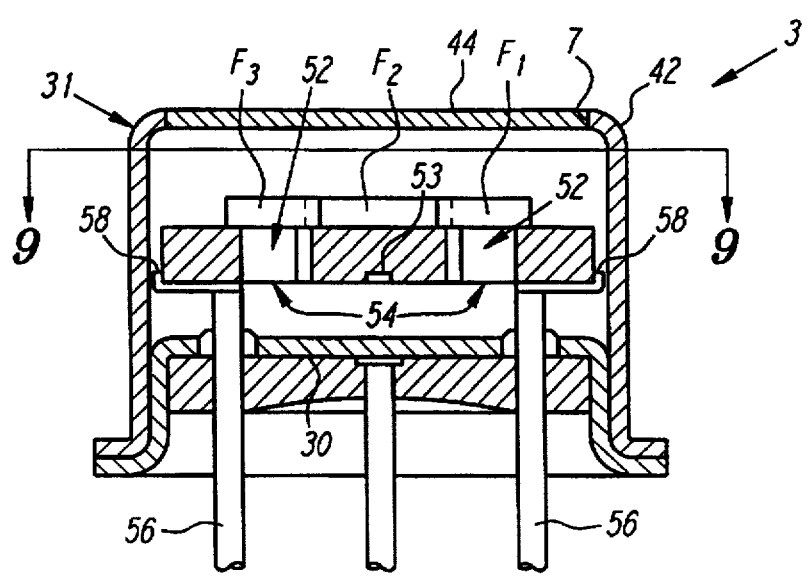
FIG. 10 is a longitudinal cross sectional view of a detector assembly according to the embodiment in FIG. 9 taken along line 10—10.
Figure 13:
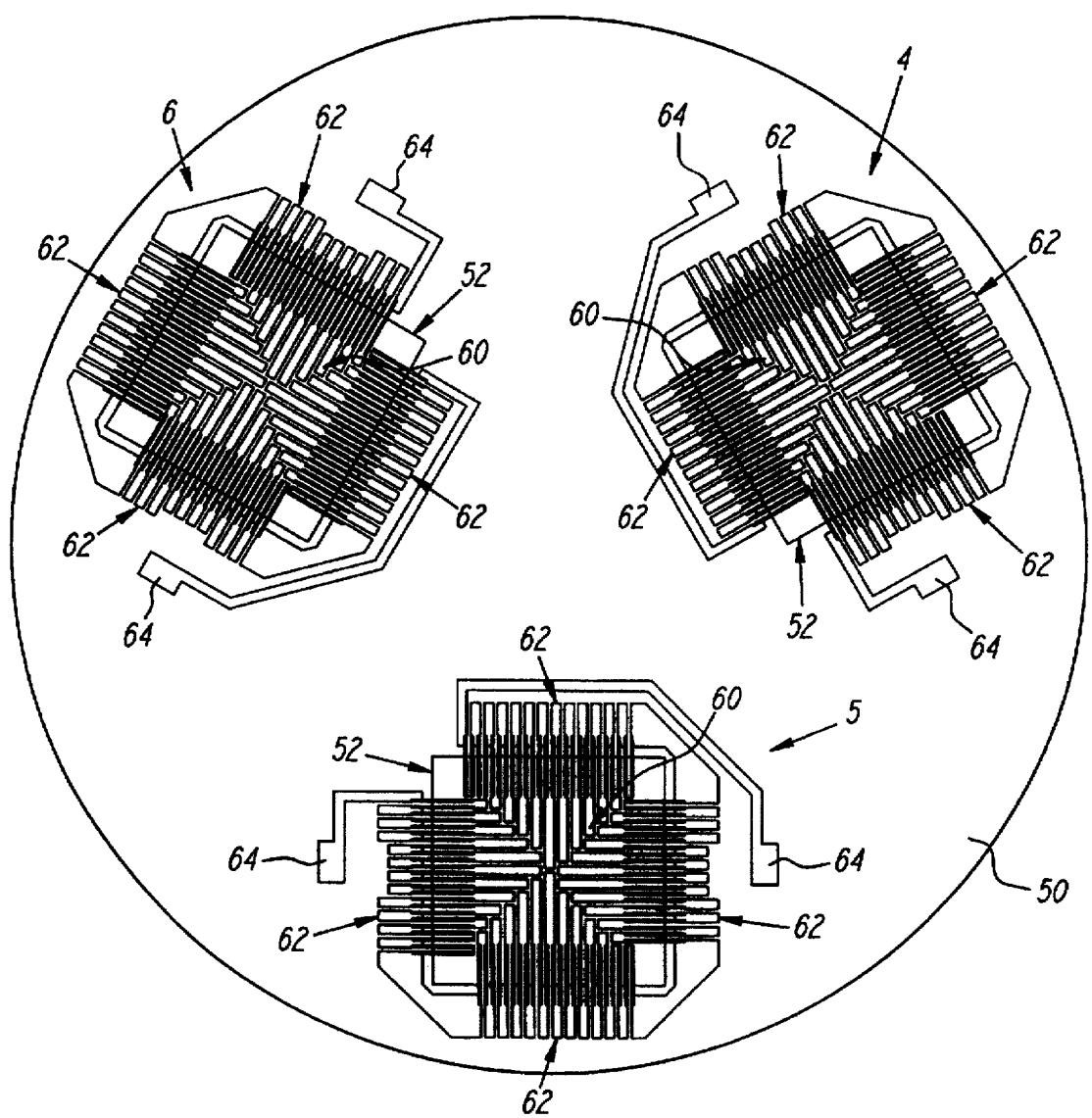
FIG. 13 is an enlarged bottom view of the substrate used in the detector assembly embodiment illustrated in FIGS. 9 and 10 showing thermopiles manufactured thereon.

A particularly preferred detector assembly 3 is now described in connection with FIGS. 9–16. As illustrated in FIGS. 9, 10 and 13, detector assembly 3 includes three infrared detectors 4, 5, and 6 that have been formed on substrate 50 mounted within detector housing 31. Detector housing 31 is preferably a TO-5 can, comprised of a housing base 30, and a lid 42. Lid 42 includes an aperture collar 7 which defines a port for receiving radiation into the detector assembly. The FOV of the detector assembly 3 is, therefore, limited by the aperture collar 7. Lid 42 also preferably includes a light transmissive window 44 which fits within or covers the port defined by the aperture collar 7. Light transmissive window 44 is bonded to the lid 42 so that when lid 42 is attached to base 30, infrared detectors 4, 5, and 6 are hermetically sealed within detector assembly 3.

Infrared detectors 4, 5, and 6 are supported on a substrate 50 which, in the present embodiment, is made out of a semiconductor material such as Si, Ge, GaAs or the like. Because of their close proximity, the field of view of detectors 4, 5, and 6 overlap substantially.

In the present embodiment, infrared detectors 4, 5, and 6 are preferably thin film or silicon micromachined thermopiles. Thermopiles 4, 5, and 6 each span an aperture 52 formed in the substrate 50. Apertures 52 function as windows through which the radiation that is passed by bandpass filters $F_1$, $F_2$, and $F_3$ is detected. As is well known in the art, thin film or micromachined thermopile detectors 4, 5, and 6 are manufactured on the bottom side of substrate 50 and may employ any of a number of suitable patterns. FIG. 13 is an enlarged view of the bottom side of substrate 50 and illustrates one suitable pattern that could be employed for thin film or micromachined thermopile detectors 4, 5, and 6. A top view of substrate 50 is provided in FIG. 12.

As is typical in the art, the hot junctions 60 of each of the thermopile detectors 4, 5, and 6 are preferably supported on a thin electrically insulating diaphragm 54 that spans each of the apertures 52 formed in substrate 50 and the cold junctions 62 are positioned over the thick substrate 50. While the three apertures 52 are preferably spanned by a thin electrically insulating diaphragm 54, the thermopile detectors can also be self-supporting.

In operation, infrared radiation from the passive infrared source enters the detector housing 31 through window 44. The infrared radiation then strikes interference bandpass filters $F_1$, $F_2$, and $F_3$, each of which passes radiation within a predefined spectral band. The radiation passing the interference filters $F_1$, $F_2$, and $F_3$, then strikes the diaphragm 54, or hot junctions 60 if the thermopiles are self-supporting, where it is detected by infrared thermopile detectors 4, 5, and 6, respectively.

To improve the sensitivity of detectors 4, 5, and 6 to incident radiation, the top side of the electrically insulating diaphragm 54 can be coated with a thin film of bismuth oxide or carbon black during packaging so that the aperture areas absorb incident radiation more efficiently. If the thermopile detectors 4, 5, and 6 are self-supporting, then the side of hot junctions 60 upon which radiation is incident can be coated with bismuth oxide or carbon black directly.

By positioning the cold, or reference, junctions 62 over the thick substrate 50, the reference junctions of each of the detectors are inherently tied to the same thermal mass. Substrate 50, therefore, acts as a heat sink to sustain the temperature of the cold junctions 62 of each of the detectors at a common temperature. In addition, substrate 50 provides mechanical support to the device.

Although the present embodiment has been described as a single substrate 50 with three infrared thermopile detectors 4, 5 and 6 formed thereon, as one skilled in the art would recognize, three separate substrates each having one infrared thermopile detector manufactured thereon could be used in place of the substrate 50 described in the present embodiment.

Electrically insulating diaphragm 54 may be made from a number of suitable materials well known in the art, including a thin plastic film such as MYLAR®, which is a trademark for polyester film, or an inorganic dielectric layer such as silicon oxide, silicon nitride, or a multilayer structure comprised of both. Preferably the electrically insulating diaphragm 54 is a thin inorganic dielectric layer because such layers can be easily fabricated using well known semiconductor manufacturing processes, and, as a result, more sensitive thermopile detectors can be fabricated on substrate 50. Moreover, the manufacturability of the entire device is improved significantly. Also, by employing only semiconductor processes to manufacture detectors 4, 5, and 6, substrate 50 will have on-chip circuit capabilities characteristic of devices based on the full range of silicon integrated circuit technology; thus, the signal processing electronics for detectors 4, 5, and 6 can, if desired, be included on substrate 50.

A number of techniques for manufacturing thermopile detectors 4, 5, and 6 on the bottom side of substrate 50 are well known in the thermopile and infrared detector arts. One method suitable for producing thermopile detectors 4, 5, and 6 using semiconductor processing techniques is disclosed in U.S. Pat. No. 5,100,479, issued Mar. 31, 1992, hereby incorporated by reference.

Referring to FIGS. 10 and 13, output leads 56 are connected to the output pads 64 of each of the thermopile detectors 4, 5, and 6 at bonding regions 58 using solder or other well known materials. Because the reference junctions of detectors 4, 5, and 6 are thermally shunted to one another, it is possible for the reference junctions for each of the detectors 4, 5, and 6 to share a common output pad. As a result, only four output leads would be required rather than six to communicate the output of the detectors. The output leads 56 typically connect the detectors 4, 5, and 6 to signal processing electronics. As mentioned above, however, the signal processing electronics can be included directly on substrate 50 in which case output leads 56 would be connected to the input and output pads of the signal processing electronics, rather than the output pads from the infrared thermopile detectors 4, 5, and 6.

As illustrated in FIG. 10, a temperature sensing element is preferably constructed on substrate 50 near cold junctions 62 of one of the thermopile detectors. The temperature sensing element monitors the temperature of substrate 50 in the area of the cold junctions and thus the temperature it measures is representative of the temperature of the cold junctions 62. The output from the temperature sensing element 53 is communicated to the signal processing electronics so that the signal processing electronics can compensate for the influence of the ambient temperature of the cold junctions of the thermopile detectors. Temperature sensing element 53 is preferably a thermistor, but other temperature sensing elements can also be used such as diodes, transistors, and the like.

Figure 11:
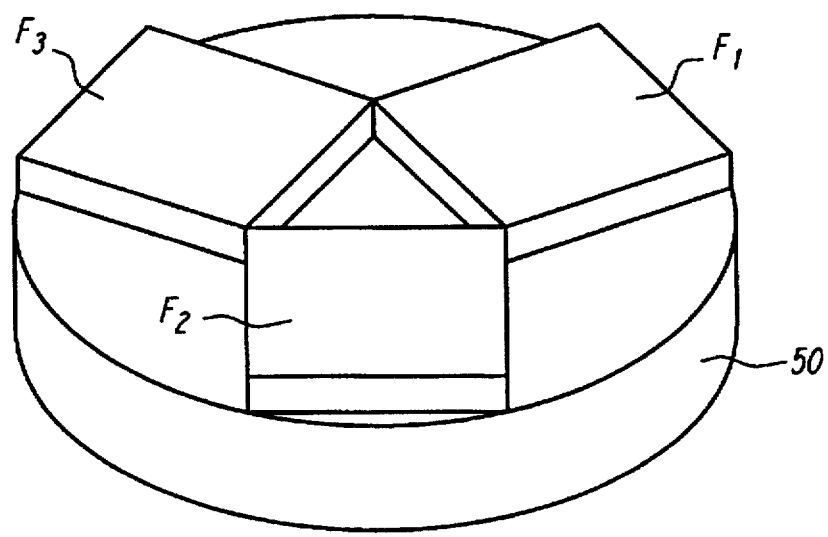
FIG. 11 is an oblique view of the substrate and interference bandpass filters depicted in FIGS. 9 and 10.
Figure 12:
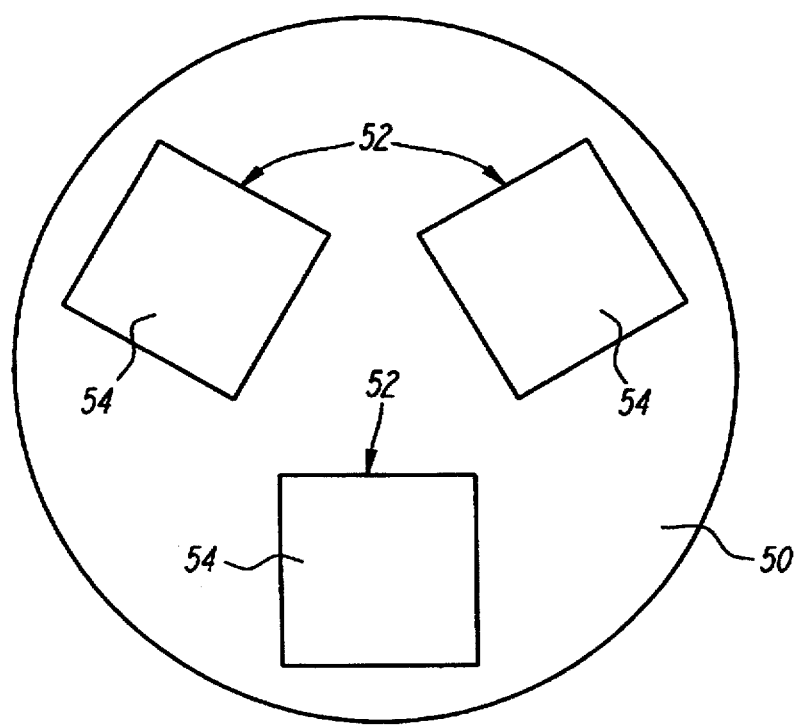
FIG. 12 is a top view of the substrate used in the detector assembly embodiment illustrated in FIGS. 9 and 10.

Referring now to FIGS. 9–11, interference bandpass filters $F_1$, $F_2$, and $F_3$ are mounted on the top of substrate 50 so that they each cover one of the apertures 52 in substrate 50. The CWL and FWHM of bandpass filters $F_1$, $F_2$, and $F_3$ are set as described in connection with FIGS. 1–3 above. Because the interference filters cover apertures 52, light entering detector assembly 3 through window 44 must first pass through filter $F_1$, $F_2$, or $F_3$ before reaching infrared detector 4, 5, or 6, respectively. Thus, by employing three separate apertures in substrate 50, light passing through one of the filters is isolated from the light passing through one of the other filters. This prevents cross talk between each of the detector channels. Therefore, the light that reaches infrared detectors 4, 5, and 6 from the passive infrared source 8 is the light falling within the spectral band intended to be measured by the particular detector.

Preferably the filters $F_1$, $F_2$, and $F_3$ are secured to substrate 50 using a thermally conductive material, such as thermally conductive epoxy. An advantage of securing the filters to substrate 50 with a thermally conductive material is that it improves the thermal shunting between the filters and the substrate, which is at the same temperature as the reference, or cold, junctions 62 of the thermopile detectors 4, 5, and 6. As a result, the background noise from the interference filters is minimized.

As interference bandpass filters $F_1$, $F_2$, and $F_3$ are each above 0K they give off a certain amount of infrared radiation. The total radiant flux incident at a detector due to its filter, which normally has a temperature close to that of ambient, is a function of how well the filter is thermally shunted to the reference or cold junctions 62 of the detector. This takes into consideration how a thermopile works. Namely, the output voltage generated by a thermopile is a direct measure of the difference in temperature between the signal (hot) junctions and the reference (cold) junctions of the thermocouples which make up the thermopile. A thermopile is nothing more than a large number of thermocouples wired in series to increase the output voltage of the device. Thus, how well a filter is thermally shunted to the reference junctions of its thermopile detector can effect the output voltage of the detector.

In the worst case, when the filter is not thermally shunted to the reference junctions at all, the radiant flux incident at the thermopile detector includes an undesirable bias from the filter that diminishes the modulation of the desired signal from the passive infrared source 8 that passes through the filter from the outside to the hot junctions of the thermopile. The ratio of the useable to the non-useable signal at the hot junctions is given by the ratio of the spectral radiant emittance of the passive infrared source 8 at the spectral band passed by the interference filter to the spectral radiant emittances given off by the filter at all wavelengths. At 295K, this could be as small as $2.3 \times 10^{-3}$ for an interference filter having a CWL of 4.67 μm and a FWHM of 0.2 μm. However, in actual situations, the filter is always somewhat shunted to the reference electrode of the thermopile detector and the ratio of useable signal to the non-useable signal is around 0.1 to 0.2.

The present detector assembly embodiment specifically eliminates, as much as possible, the unwanted radiant flux coming at the thermopile detector from the filter. This is done by providing a very efficient thermal shunt between the reference (cold) junctions 62 of the thermopile detectors 4, 5, and 6 and their corresponding interference filters $F_1$, $F_2$, and $F_3$. This in effect nulls out the influence of the filter to the signal (hot) junctions 60 of the detector, thus rendering the radiation passed by the filters from the passive infrared source 8 the only source of the radiation that is measured by the thermopile detectors. Needless to say, this is the only radiation that is important, and it is now usefully isolated for processing by the thermopile detector.

Figure 14:
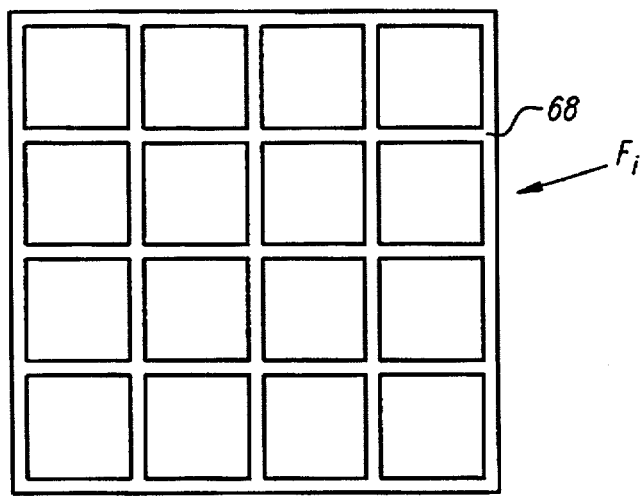
FIG. 14 is an illustration of a preferred construction of an interference bandpass filter for use in detector assemblies according to the present invention.
Figure 15:
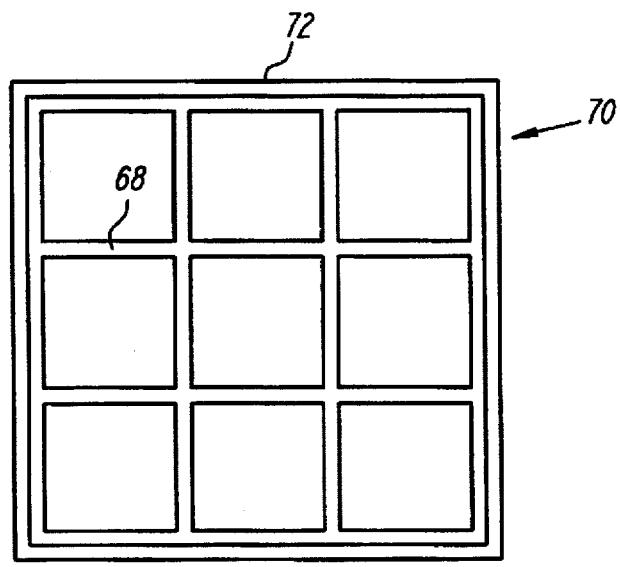
FIG. 15 is an illustration of a filter mounting fixture for use in detector assemblies according to the present invention.
Figure 16:
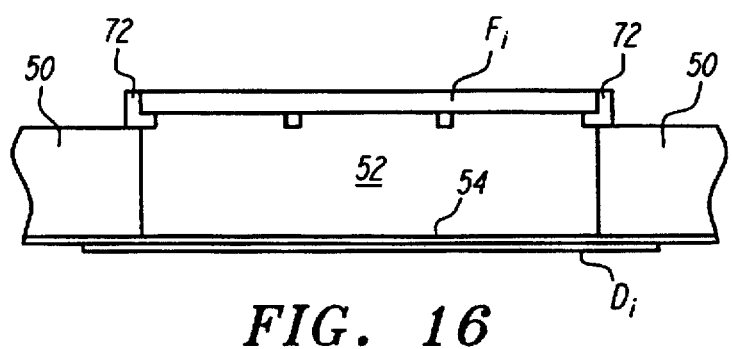
FIG. 16 is a partial cross sectional view through the substrate illustrated in FIGS. 9–11 showing the filter mounting fixture of FIG. 15 in actual use.

To further improve the thermal shunt between the filters and the substrate 50, additional heat sink means can be provided. Thus, for example, a heat sinking metallic grid 68 can be deposited on one or both sides of the interference filters $F_i$ as shown in FIG. 14. The metal used for the grid should have a high thermal conductivity. Gold is particularly well suited for this purpose. Alternatively, as shown in FIGS. 15 and 16, a heat sinking metallic grid 68 can be incorporated into a mounting fixture 70. The thermal conductivity of metallic grid 68 can be improved by coating the grid with gold. Mounting fixture 70 comprises a grid portion 68 and a raised lip portion 72. Interference filter $F_i$ (corresponding to filters $F_1$, $F_2$, or $F_3$) sits in the recess formed by the raised lip 72. To improve the heat transfer between the mounting fixture 70 and filter $F_i$, filter $F_i$ is preferably bonded to mounting fixture 70 using a thermally conductive material, such as thermally conductive epoxy. The mounting fixture is then bonded, using a thermally conductive material, to the top of substrate 50 to cover aperture 52. This is illustrated in FIG. 16 which is a partial cross sectional view through substrate 50 at one of the thermopile detectors $D_i$ corresponding to detectors 4, 5, or 6.

Figure 17:
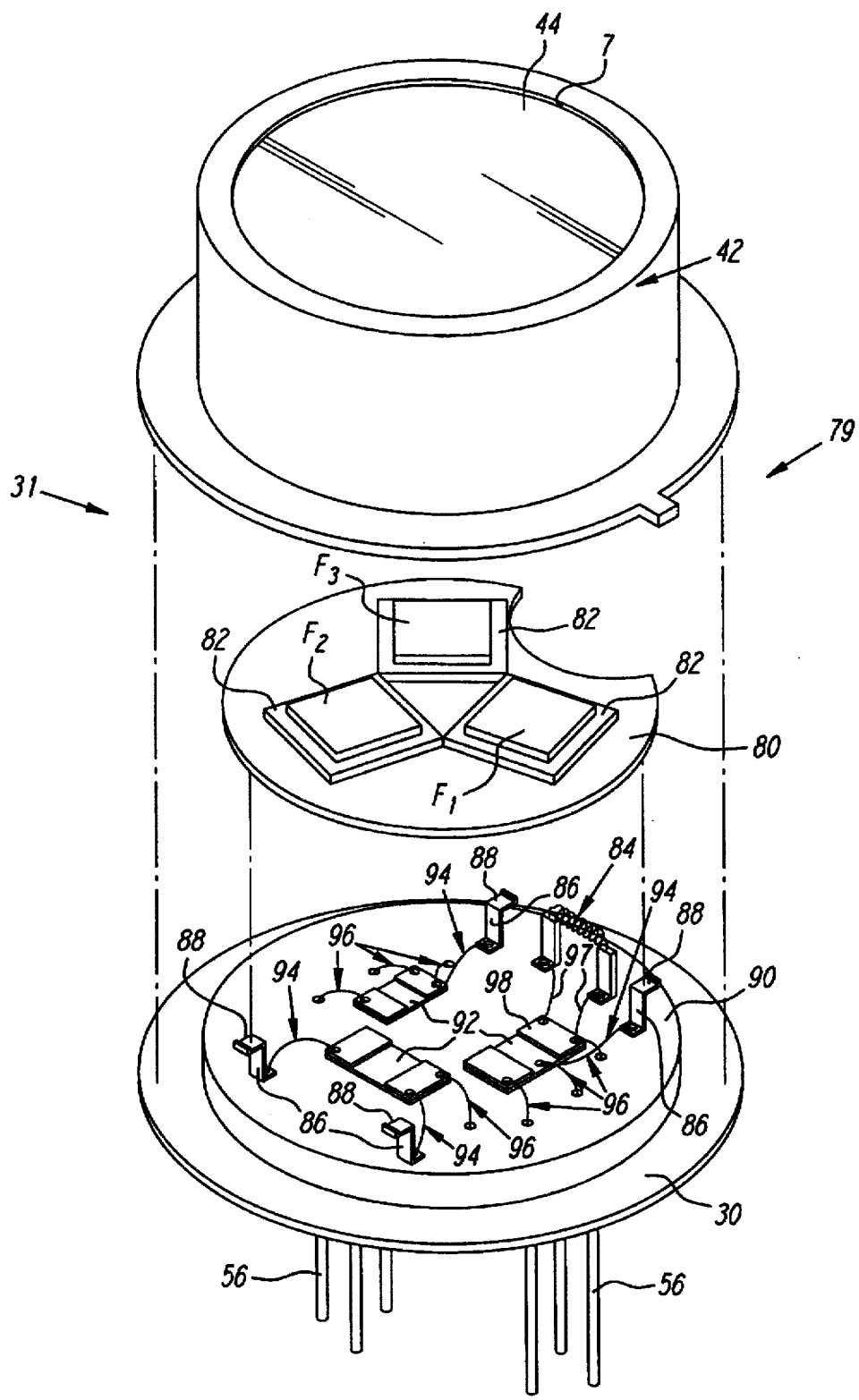
FIG. 17 is an exploded view of a detector assembly according to another embodiment of the present invention.
Figure 18:
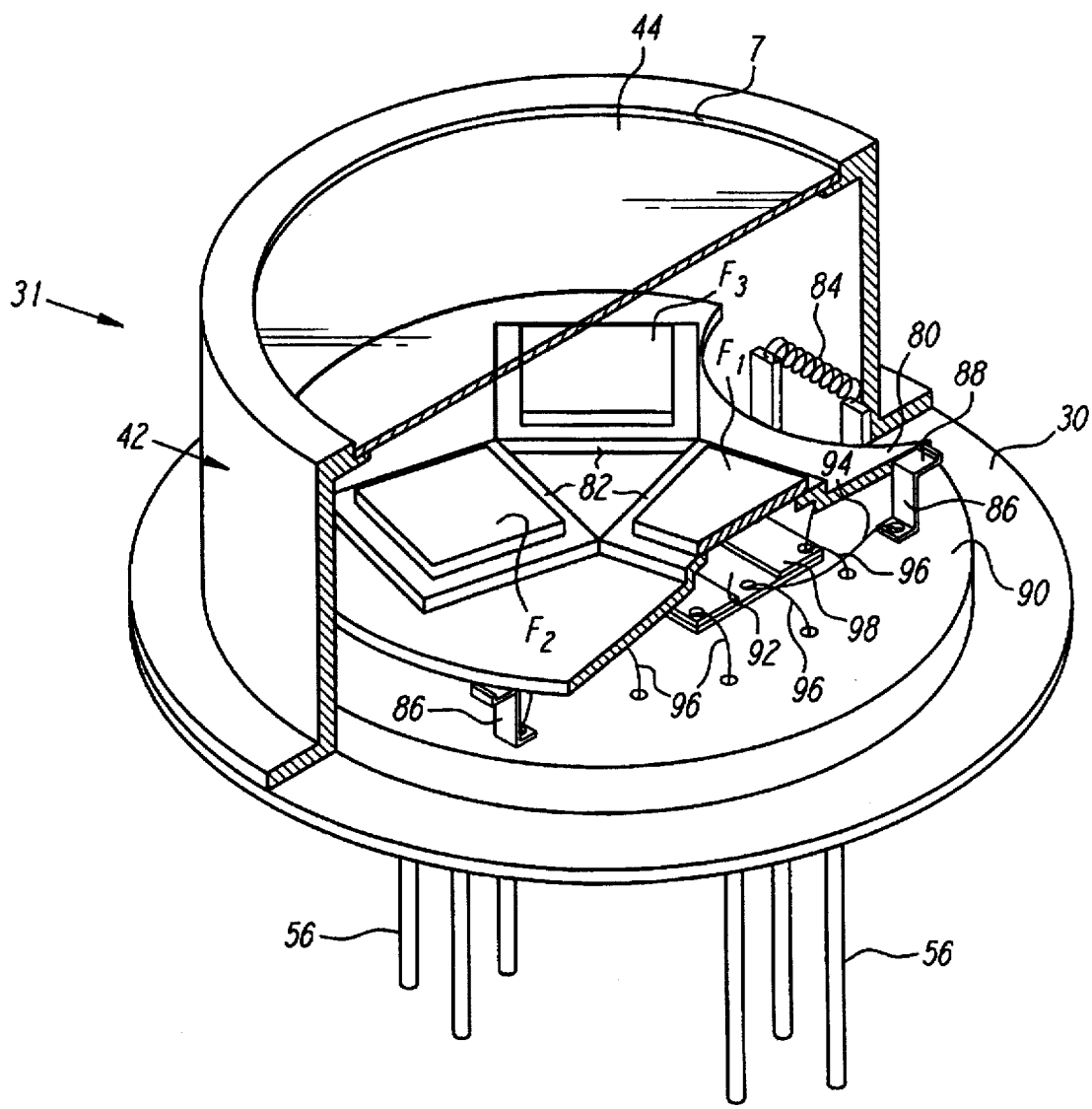
FIG. 18 is an oblique view showing a partial cutaway of the detector assembly illustrated in FIG. 17.

Another particularly preferred detector assembly 79 is now described in connection with FIGS. 17 and 18. Detector assembly 79 includes three infrared detectors 4, 5, and 6 (not shown) formed on semiconductor substrate 80 mounted within detector housing 31. Infrared detectors 4, 5, and 6 are thin film or micromachined infrared thermopile detectors formed on the bottom side of substrate 80 as described in connection with the detector assembly embodiment illustrated in FIGS. 9–13. The primary difference between substrate 80 of the present embodiment and substrate 50 of the embodiment illustrated in FIGS. 9–13 is that substrate 80 includes a raised rim 82 surrounding each of the three apertures 52 formed in the substrate. Raised rims 82 provide additional thermal mass to maintain the temperature of the reference (cold) junctions of the thermopiles 4, 5, and 6 at the same temperature. The added thermal mass is desirable in the present embodiment, because the detector assembly 79 according to the present embodiment also includes an active infrared light source 84 operatively mounted within the detector housing 31.

As with the embodiment illustrated in FIGS. 9–13, a temperature sensing element 53 (not shown) is preferably constructed on substrate 50 near the cold junctions of one of the thermopile detectors in order to monitor the temperature of the cold junctions and provide that information to the signal processing electronics.

Infrared light source 84, provides added flexibility to detector assembly 79. Namely, it permits the three channel detector assembly 79 to be used in a traditional NDIR gas sensor having an active infrared light source, or, alternatively, if infrared light source 84 is disabled, detector assembly 79 can be used in a passive infrared gas sensor according to the present invention. When detector assembly 79 is used in an NDIR gas sensor the added thermal mass provided by the raised rims 82 helps maintain the temperature of the reference junctions at as uniform of temperature as possible when the active infrared light source 84 is cycling on and off. This is helpful in maintaining the sensitivity of the detectors to the modulation in their signal due to the presence of a gas, or gases, being monitored in the sample path of the detectors.

Detector housing 31 in the present embodiment is a TO-5 can, comprised of a housing base 30, and a lid 42. Lid 42 includes an aperture collar 7 which defines a port for receiving radiation into the detector assembly. The FOV of the detector assembly 79 is limited by the aperture collar 7. Because of their close proximity, the FOV of detectors 4, 5, and 6 overlap substantially. Lid 42 also preferably includes a light transmissive window 44 which fits within or covers the port defined by the aperture collar 7. Light transmissive window 44 is bonded to the lid 42 so that when lid 42 is attached to base 30, infrared detectors 4, 5, and 6 are hermetically sealed within detector housing 31.

The material used for window 44 should be selected as described in connection with the detector assembly embodiments illustrated in FIGS. 4 and 5 and 9–16.

Interference bandpass filters $F_1$, $F_2$, and $F_3$ are mounted on the top of raised rims 82 so that they each cover one of the apertures 52 in substrate 80. The CWL and FWHM of bandpass filters $F_1$, $F_2$, and $F_3$ are set as described in connection with FIGS. 1–3 above. Because the interference filters cover apertures 52, light entering detector housing 31 through window 44 must first pass through filter $F_1$, $F_2$, or $F_3$ before reaching infrared detector 4, 5, or 6, respectively. Thus, by employing three separate apertures in substrate 80, light passing through one of the filters is isolated from the light passing through one of the other filters. This prevents cross talk between each of the detector channels. Therefore, the light that reaches infrared detectors 4, 5, and 6 from the passive infrared source 8—or from the active infrared source 84 if the detector assembly is being used in a conventional NDIR gas sensor—is the light falling within the spectral band intended to be measured by the particular detector.

Interference bandpass filters $F_1$, $F_2$, and $F_3$ are bonded to the top of raised rims 82 surrounding apertures 52 using a thermally conductive material, such as thermally conductive epoxy. An advantage of securing the filters to the raised rims 82 with a thermally conductive material is that it improves the thermal shunting between the filters and the substrate 80, which is at the same temperature as the reference, or cold, junctions of the thermopile detectors 4, 5, and 6. As a result, the background noise from the interference filters is minimized.

To further improve the thermal shunt between the filters and the substrate 80, a heat sinking metallic grid 68 can be deposited on one or both sides of the interference filters $F_i$ as shown in FIG. 14. The metal used for the grid should have a high thermal conductivity. Gold is particularly well suited for this purpose. Alternatively, as shown in FIG. 15, a heat sinking metallic grid 68 can be incorporated into a filter mounting fixture 70. Mounting fixture 70 comprises a grid portion 68 and a raised lip portion 72. As illustrated in FIG. 16, an interference filter $F_i$ (corresponding to filters $F_1$, $F_2$, and $F_3$) sits in the recess formed by the raised lip 72. To improve the heat transfer between the mounting fixture 70 and filter $F_i$, filter $F_i$ is preferably bonded to mounting fixture 70 using a thermally conductive material, such as thermally conductive epoxy. The mounting fixture is then bonded, using a thermally conductive material, to the top of one of the raised rims 72 to cover aperture 52.

Substrate mounting fixtures 86 are connected to the output pads (not shown) of each of the thermopile detectors 4, 5, and 6 at bonding regions 88 using solder or other well known materials. As the reference junctions of the detectors 4, 5, and 6 share a common output pad in the present embodiment, only four substrate mounting fixtures 86 are required to communicate the outputs of the detectors. Substrate mounting fixtures 86 are insulated from the base 30 of detector housing 31 because they are mounted on an electrically insulative substrate 90, which is preferably made out of a material selected from the group consisting of aluminum oxide and beryllium oxide. The output signal from detectors 4, 5, and 6 is communicated through substrate mounting fixtures 86, via wire bonds 94, to the signal processing electronics 92. Signal processing electronics 92 can comprise a plurality of microchips diebonded to insulative substrate 90 or a single microchip diebonded to insulative substrate 90. Output leads 56 are connected to the input and output of the signal processing electronics 92 via wire bonds 96.

Signal processing electronics 92 includes a source driver 98 for driving active infrared source 84 at a known frequency. Source driver 98 drives active infrared source 84 through wire bonds 97. The manner in which active infrared source 84 should be driven by source driver 98 for conventional NDIR applications is well known in the art and need not be explained further herein.

Although detector assembly 79 has been illustrated as including signal processing electronics 92 diebonded on insulative substrate 90, signal processing electronics 92 could be incorporated directly on semiconductor substrate 80. Alternatively, to simplify detector assembly 79, output leads 56 could be connected directly to the outputs of detectors 4, 5, and 6 using solder or other well known materials. The output leads 56 would, in this situation, connect the outputs of infrared thermopile detectors 4, 5, and 6 to signal processing circuitry on the exterior to the detector assembly 79.

If detector assembly 79 is used in a passive infrared gas sensor according to the present invention, infrared radiation from the passive infrared source 8 enters the detector housing 31 through window 44. The infrared radiation then strikes interference bandpass filters $F_1$, $F_2$, and $F_3$, each of which passes radiation within a predefined spectral band. The radiation passing the interference filters $F_1$, $F_2$, and $F_3$, then strikes the inorganic dielectric membrane (not shown) spanning each of the apertures, or hot junctions if the thermopiles are self-supporting, where it is detected by infrared thermopile detectors 4, 5, and 6, respectively. The outputs from each of the detectors is then communicated to the signal processing electronics where it is processed in accordance with the description of the passive infrared gas sensor provided above in connection with FIGS. 1–3.

As with the detector assembly 3 described in connection with FIGS. 9–16, the sensitivity of detectors 4, 5, and 6 to incident radiation can be improved by coating the top side of the dielectric membrane (not shown) with a thin film of bismuth oxide or carbon black during packaging so that the aperture areas absorb incident radiation more efficiently. If the thermopile detectors 4, 5, and 6 are self-supporting, then the side of the hot junctions upon which radiation is incident can be coated with bismuth oxide or carbon black directly.

As indicated above, because detector assembly 79 also includes an active passive infrared source, it can be utilized in an NDIR gas sensor. The use of detector assembly 79 in an NDIR gas sensor according to the present invention is described in detail below.

Figure 6:
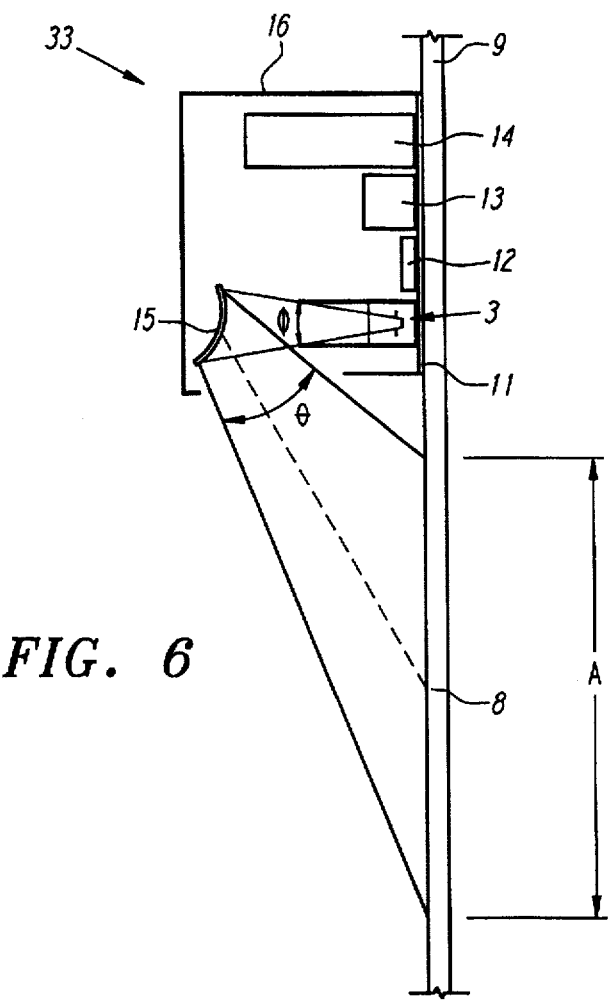
FIG. 6 shows an alternate preferred embodiment for the current invention depicting the actual use of a portion of a wall as the "passive" infrared source and the use of a convex spherical reflector to increase the original field of view (FOV) of the detector assembly.

FIG. 6 shows the actual implementation of a preferred embodiment of a PIA gas sensor 33 according to the present invention. The detector assembly 3 is mounted directly on the printed circuit board (PCB) 11 which also is a mount for the signal processing electronics 12, siren 13 for sounding an alarm and a battery power source 14. Battery power source 14 is preferably a lithium battery, which should provide sufficient power to operate the system from 1 to 2 years. Although the present PIA gas sensor is illustrated as employing detector assembly 3, detector assembly 79 described in connection with FIGS. 17 and 18 can also be employed in the present embodiment.

Spherical reflector 15, which is affixed rigidly to the detector assembly 3, is used to increase the FOV of the detector assembly 3. The sample path length for the gas sensor in this case is again defined by the distance between the detector assembly 3 and the passive infrared source 8, which is defined as a portion of the wall 9. The PCB 11 carrying all the components described earlier is housed in an enclosure 16 for protection from handling and external environments when being used to implement the PIA technique of the present invention.

As one skilled in the art would recognize, the FOV of detector assembly 3 can similarly be enhanced by using a refractive optics system instead of reflective optics system. Reflective optics are preferred, however, because of their cost.

Figure 7:
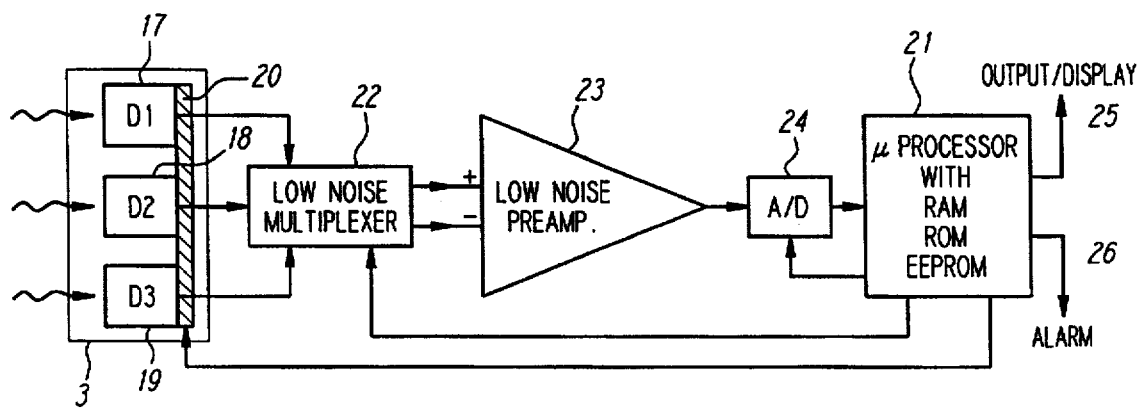
FIG. 7 shows a schematic drawing for the signal processing circuits for a preferred embodiment of the present invention.

FIG. 7 shows the schematic drawing for the signal processing circuits according to a preferred embodiment for the present invention. The signal processing circuits illustrated in FIG. 7 can be used in conjunction with any of the detector assembly embodiments described above.

According to the present embodiment, infrared radiation emanating from the passive source (not shown) is collected within the FOV of the detector assembly 3 onto detectors 17, 18 and 19 representing respectively the signal detector $D_1$, and the neutral detectors $D_2$ and $D_3$. The detectors 17, 18 and 19 are thermopile detectors and their reference junctions are tied thermally to the same heat sink 20. One of the major advantages of the thermopile detectors is their linear output (scalable linearly with temperature from 0° to 70° C.). Thus, the outputs of the detectors 17, 18 and 19 can be corrected for environmental temperature changes by sensing the same at the common reference junction heat sink 20 using microprocessor 21.

Although the present embodiment is illustrated as employing detector assembly 3, detector assembly 79 described in connection with FIGS. 17 and 18 can also be employed in the present embodiment.

In order to minimize DC drifts, each of the three detectors outputs are subsequently switched with the same duty factor by a low noise multiplexer 22 controlled by the microprocessor 21 to the differential input of the same low noise preamplifier 23. The amplified signals are then converted by an A/D converter 24 before being fed into the microprocessor 21 for signal processing. After the gas to be measured is detected, the concentration of the gas can be monitored based on a predetermined function programmed into microprocessor 21. The concentration can be outputted or displayed using cable 25 or in some cases an alarm signal can also be generated by the microprocessor 21 using cable 26.

Microprocessor 21 is of the low power type and contains enough RAM, ROM and EEprom for appropriately processing the signals originated by the detector assembly 3.

The versatility of the passive infrared gas detectors of the present invention could be further enhanced by adding a distance measuring device to the gas detector. This would permit the user to quickly and easily modify the sample length S depending on the application. The distance measuring device could be of the contact or non-contact type. For example, it could comprise a laser diode with a sensor as is well known in the art. The output of the distance measuring device would be communicated to the signal processor so that the appropriate sample path length S can be inserted into Equation [1] when calculating the concentration of the gas. As discussed above, the change in the path length is not required for calculating the ratio of the outputs from the two neutral channels, because this factor would cancel out since it would be the same for both detectors.

Alternatively, the gas detector can include a switch so that the user can enter preset pathlengths. For example, the switch might include path length settings increasing by one foot increments so that the user can measure and enter the appropriate path length for the set up in which the gas detector of the present invention is being used. The selection of a particular path length is communicated to the microprocessor 21 so that it knows the appropriate path length to use in calculating the concentration of the gas in the sample volume.

For slightly more flexibility, a data entry pad can be used so that the user can enter any desired path length and the microprocessor 21 will compensate accordingly during its calculations.

Figure 8:
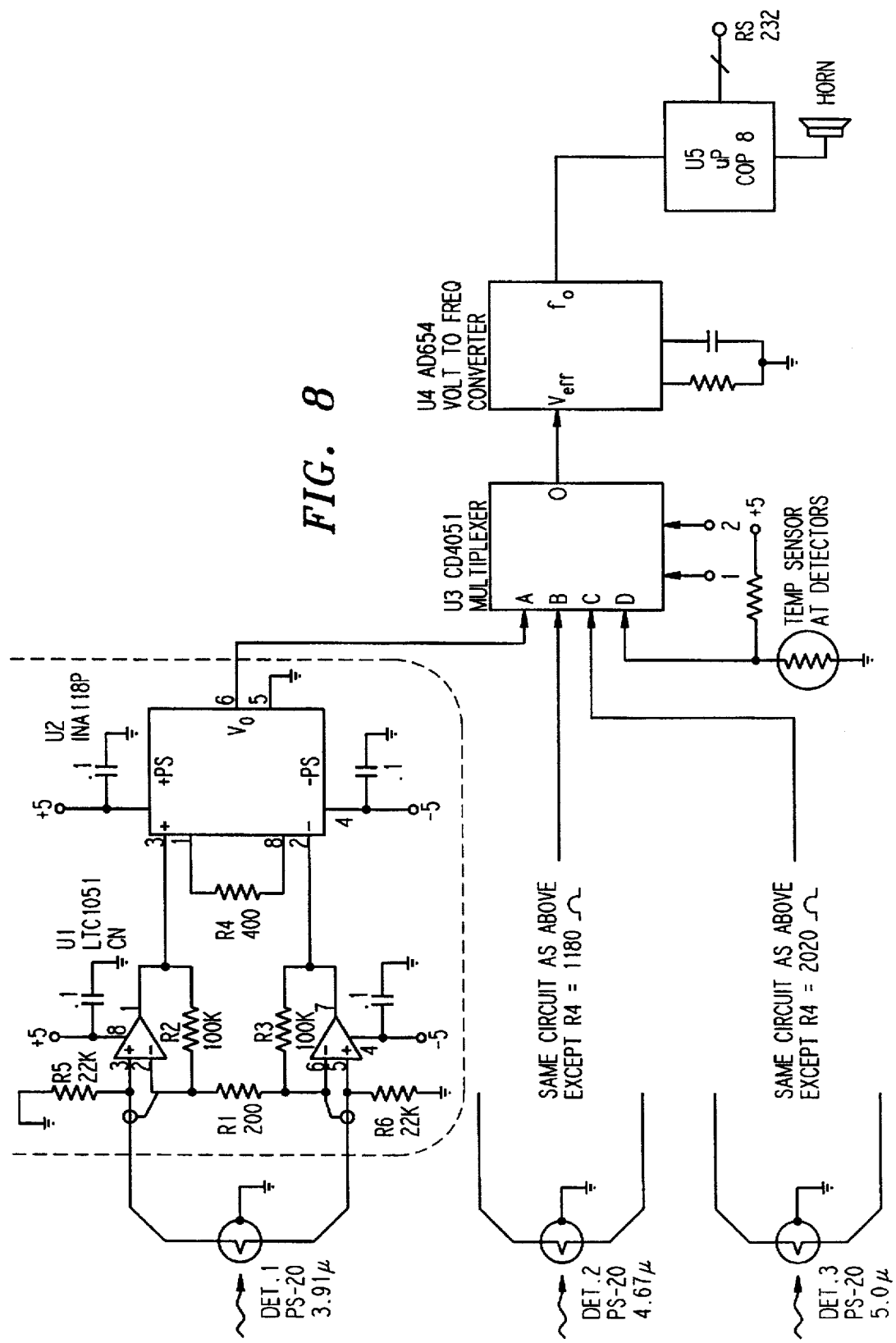
FIG. 8 shows the circuit schematic for the signal processor according to another embodiment of the present invention.

FIG. 8 is a circuit schematic for a signal processor according to another embodiment of the present invention. The structure of the circuit is determined by the low level of the expected signals, in the order of 5 to 85 µVolt. There are three identical preamplifier circuits which differ only in the value of a gain setting resister, R4. The amplifiers are constructed in the form of instrumentation, amplifiers which have a very high common mode signal rejection, because for operation in the home near 60 Hz power wiring large signals may be induced magnetically. Magnetic shielding of the detectors and circuits should reduce this. The detectors and circuit components should also be protected from rapid temperature changes which can produce thermocouple signals in the components. The thermal and mechanical design are very important to allow the full capabilities of the electronic circuit.

U1 forms the input part of the instrumentation amplifier. It was selected for its very low input offset voltage, about 0.5 µV, and very low change of that voltage with temperature. For high common mode rejection the two feedback resistors R2 and R3 should be matched to better than 0.1%, and should have temperature coefficients of 10 ppm/deg C. or better. The gain of this circuit is determined by the ratio of R2 and R3 to R1, about 500. The noise level for dc to 10 Hz is about 2 µV pp. This is higher than is desirable, but it can be filtered later. The low input offset and drift with temperature are more important to obtain proper processing of the sampled outputs.

The input noise level of the output part of the circuit is much lower, about 0.28 µV, but the offset is much higher, about 50 uV, and with a larger temperature coefficient. U2 is actually another instrumentation amplifier. It is used to provide a stable high gain of about 400. It is used because it is less expensive than another amplifier and four accurate gain setting resistors. The expected output is from one to two volts or more, depending on the input radiation to the detector. The gains of the preamps for the other two detectors are lower since more radiation is expected at the longer wavelengths of those detectors.

The rest of the signal processing could be handled in many different ways, one implementation is shown as an example. The three signal channels and one temperature sensor near the detectors are selected by a multiplexer, and their value converted to a frequency by a voltage to frequency converter. The frequency output can be processed easily by a microprocessor ($\mu P$), to determine the temperature of the scene viewed, the temperature of the detectors, and then the absorption due to CO gas, or other gas to be measured, from the expected signals at those temperatures.

Figure 19:
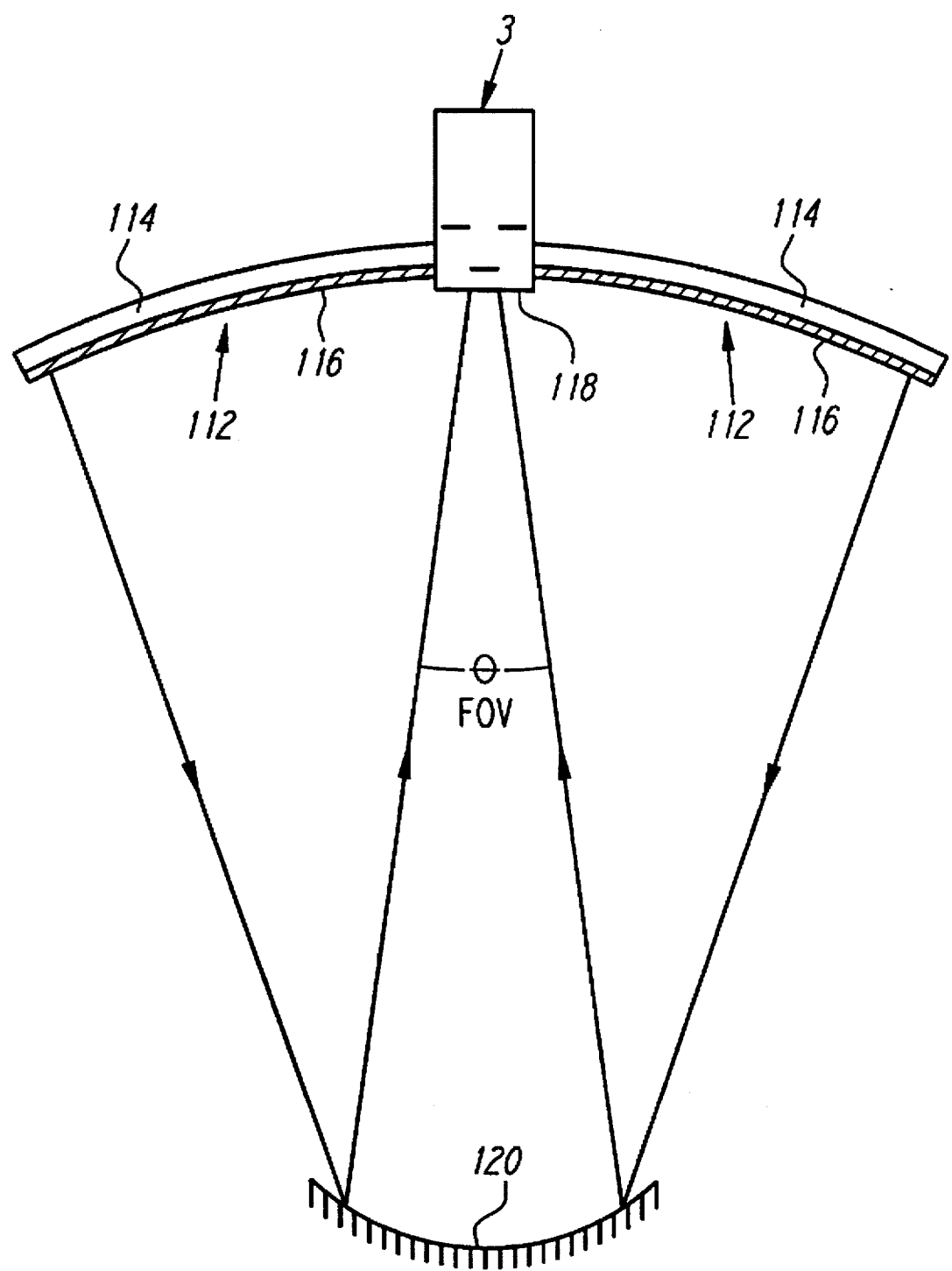
FIG. 19 is a passive infrared analysis gas sensor according to another embodiment of the present invention.

Another embodiment of a PIA gas sensor according to the present invention is described in connection with FIG. 19. Passive infrared gas sensor 110 illustrated in FIG. 19 comprises a passive infrared source 112, a three channel infrared detector assembly 3 centered in the middle of passive infrared source 112 and having a port 118 for receiving infrared radiation therethrough, and a concave mirror 120 spaced apart from and facing the port 118 of the detector assembly 3 and the passive infrared source 112.

Passive infrared source 112 is preferably concave to increase the surface area of the infrared source within the field of view of the concave mirror 120 facing the passive infrared source. In the present embodiment, passive infrared source 112 comprises an infrared black surface 116 that has been applied to the surface of a nonconductive member 114. Infrared black surface 116 can comprise a number of materials, including black chrome oxide, bismuth oxide and carbon black. Nonconductive member 114 is comprised out of a plurality of plastic panels due to the light weight and ease of manufacture associated with plastic. As would be obvious to those skilled in the art, member 114 could also be made out of a unitary piece of plastic or other electrically insulative material.

Mirror 120 can be any concave reflective surface so as to increase the field of view of the detector assembly. Preferably, concave mirror 120 has as low of an emissivity as possible, so that all of the infrared radiation being received through port 118 in detector assembly 3 is produced by the passive infrared source 112. The concave mirror 120 should be large enough to encompass the entire field of view of the detector at the distance it is spaced apart from the detector. This can be calculated by using the equation $d=(OMxS)/2\pi^{-1/2}$, where d is the diameter of the concave mirror, OM is the solid angle subtended by the detector assembly at concave mirror 120, and S is the distance between the detector assembly and the mirror. Similarly, the passive infrared source 112 should be large enough to fill the field of view of the concave mirror.

The space between the passive infrared source and detector on one hand and the concave mirror on the other hand defines the sample chamber of the passive infrared gas sensor 110 according to the present invention. Infrared radiation emitted by the passive infrared source 112 is reflected off concave mirror 120 into detector assembly 120 through port 118. As a result, the sample path length of the passive infrared gas sensor 110 is at least twice the distance between the detector assembly 3 and the concave mirror 120. This permits the gas sensor 110 to have twice the sensitivity of passive infrared gas sensor in which the passive source is opposing the detector assembly. Alternatively, gas sensor 110 can have the same sensitivity using half the space.

Figure 20:
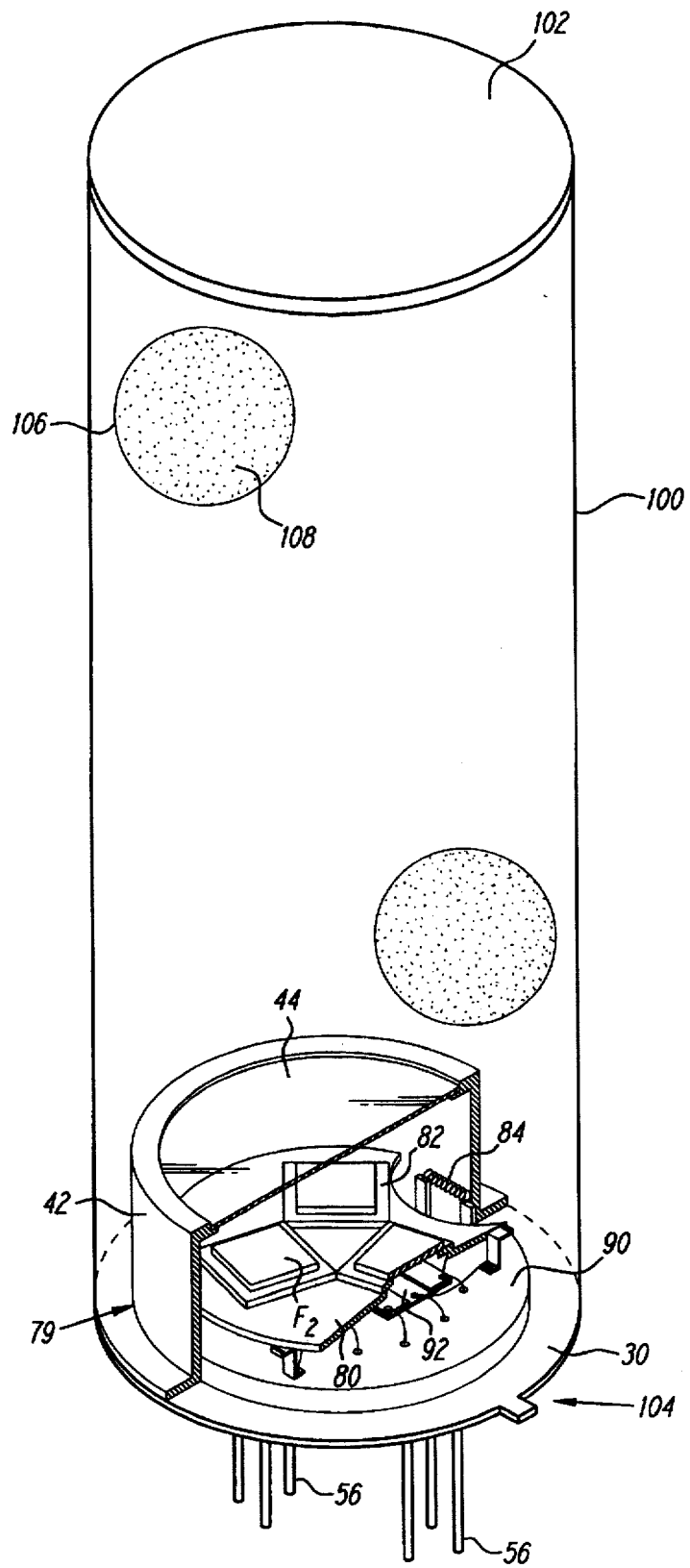
FIG. 20 illustrates the detector assembly shown in FIGS. 17 and 18 in use in an NDIR gas sensor according to the present invention.

As explained above, detector assembly 79 described in connection with FIGS. 17 and 18 also includes an active infrared source; thus, detector assembly 79 can be directly employed in an NDIR gas sensor. One potential NDIR gas sensor arrangement according to the present invention is illustrated in FIG. 20. The NDIR gas sensor of FIG. 20 comprises an elongated hollow tube 100 having a closed end 102 and an open end 104. In the preferred embodiment, the tube 100 is composed of a metal and has a circular cross section. In other embodiments, the cross section is square.

Inner surfaces of tube 100, including the inner surface of closed end 102, are specularly reflective.

In accordance with the present invention, the metal tube 100 is gastight and therefore filtering apertures, of which the filtering aperture 106 is typical, are provided at spaced locations along the tube 100 to permit the gas being monitored to enter and to leave the space within the tube. Each of the filtering apertures 106 is covered by a semipermeable membrane 108. The exact number, location, and disposition of the filtering apertures is not crucial, although some arrangements may be more optimal than others.

Three channel detector assembly 79 is mounted in the open end of hollow tube 100 in such a manner as to close off the open end and prevent gas from entering or exiting through the open end of tube 100. Because the active infrared source 84 is utilized in the present invention, detectors 5 and 6, which are used as neutral detectors to characterize the temperature of the passive infrared source 8 when the detector assembly 79 is used in a passive infrared gas sensor according to the present invention, are not required. As a result, detector assembly 79 can be used to monitor the concentration of up to three different gases in the present embodiment by simply selecting bandpass filters $F_1$, $F_2$, and $F_3$ that pass spectral bands at three different wavelengths at which three different gases to be detected strongly absorb radiation and at which other gases that might be present do not absorb. If fewer than three gases need be detected, the unneeded detector channels can be disabled. This adds a great deal of flexibility to the NDIR gas sensor according to the present invention.

The concentration of the gases to be detected within the sample chamber is determined by the extent to which they absorb radiation emitted from the active infrared source 84. By inserting detector assembly 79 into the open end of tube 100 window first as illustrated in FIG. 19, detectors 4, 5, and 6, interference bandpass filters $F_1$, $F_2$, and $F_3$, and active infrared source 84 located within detector assembly 79 are arranged so that they are all facing the inner surface of closed end 102. As a result, some of the radiation emitted by active infrared source 84 is reflected, either directly or indirectly, from the inner surface of the closed end 102 back to the detectors 4, 5, and 6 where it is detected. The amount of radiation detected at the spectral bands monitored by detectors 4, 5, and 6 can then be used to determine the concentration of the gases being monitored within the sample chamber defined by the space within tube 100 using techniques well known in the art.

The purpose of the semipermeable membrane 108 is to prevent airborne particles larger than a predetermined size from entering the space within the tube 100, while at the same time not interfering appreciably with the free diffusion of the gas to be monitored into and out of the space within the tube 100. The unwanted particles include minute droplets of moisture or oil and also include fine particulate matter such as particles of dust or smoke. If these unwanted airborne particles were to enter the space within the tube 100, they would deposit themselves onto the specularly reflective surfaces thereby reducing the reflectivity and destroying its specular nature. The unwanted particles would also deposit onto the window 44 of detector assembly 79 reducing the transmission of radiation. All of these problems are eliminated through the use of the semipermeable membrane which, in the preferred embodiment prevents airborne particles larger than 0.3 microns from entering the space within tube 100.

While the present inventions have been made clear in the illustrative embodiments, it will be immediately obvious to those skilled in the art that many modifications of structure, arrangement, proportions, elements, materials, and components used in the practice of the disclosed inventions, and otherwise, which are particularly adapted to specific environments and operative requirements, can be made without departing from the principles disclosed. For example, the detector assemblies described in connection with FIGS. 9–18 were described as being three channel detectors because they are being employed in the PIA sensor according to the present invention. However, as one skilled in the art would recognize, the detector assemblies of the present invention could be readily modified to have any number of desired channels, including one, depending on the specific application Thus, it is to be clearly understood that this description is made only by way of example and not as a limitation to the scope of the disclosed inventions as claimed below.

I claim:

1. An infrared detector assembly comprising:
   a. a detector housing having a port for receiving infrared radiation therethrough;
   b. a substrate mounted within the detector housing, the substrate having three apertures therein;
   c. a first, a second and a third thermopile detector fabricated on the bottom side of the substrate, the hot junctions of each thermopile detector positioned over one of the apertures in the substrate so as to receive radiation transmitted through the aperture, and the cold junctions of each thermopile detector positioned over the substrate;
   d. a first interference bandpass filter mounted on the top side of the substrate so that the first filter covers the aperture above the first detector and the first filter is interposed between the port and the first detector, the first interference bandpass filter designed to pass incident radiation at a first spectral band;
   e. a second interference bandpass filter mounted on the top side of the substrate so that the second filter covers the aperture above the second detector and the second filter is interposed between the port and the second detector, the second interference bandpass filter designed to pass radiation at a second spectral band; and
   f. a third interference bandpass filter mounted on the top side of the substrate so that the third filter covers the aperture above the third detector and the third filter is interposed between the port and the third detector, the third interference bandpass filter designed to pass radiation at a third spectral band.

2. An infrared detector assembly according to claim 1, further comprising output leads extending through the detector housing and electrically connected to the first, second and third thermopile detectors.

3. An infrared detector assembly according to claim 2, wherein the substrate is comprised of a semiconductor material and the first, second and third thermopile detectors are selected from the group consisting of thin film thermopile detectors and micromachined thermopile detectors.

4. An infrared detector assembly according to claim 1, wherein the substrate is comprised of a semiconductor material and the first, second, and third thermopile detectors are micromachined thermopile detectors.

5. An infrared detector assembly according to claim 4, further comprising:
   a. a signal processor fabricated on the substrate, the signal processor electrically connected to the first, second, and third thermopile detectors; and
   b. leads extending through the detector housing and electrically connected to the signal processor.

6. An infrared detector assembly according to claim 1, wherein each of the first, second, and third infrared thermopile detectors is formed on an electrically insulating diaphragm that spans the aperture the detector is positioned over.

7. An infrared detector assembly according to claim 6, wherein the electrically insulating diaphragm is comprised of a plastic film.

8. An infrared detector assembly according to claim 7, wherein the plastic film is polyester.

9. An infrared detector assembly according to claim 6, wherein the electrically insulating diaphragm is comprised of an inorganic dielectric membrane selected from the group consisting of silicon oxide, silicon nitride, and a multilayer structure of silicon oxide and silicon nitride.

10. An infrared detector assembly according to claim 1, wherein the first, second, and third interference bandpass filters are bonded to the substrate using a thermally conductive material.

11. An infrared detector assembly according to claim 10, further comprising heat sink means to improve the thermal shunt between the substrate and the first, second, and third interference bandpass filters.

12. An infrared detector assembly according to claim 1, further comprising a light transmissive window mounted within the port.

13. An infrared detector assembly according to claim 12, wherein the substrate, filters, and detectors are hermetically sealed within the detector housing.

14. An infrared detector assembly comprising:
   a. a detector housing having a port for receiving infrared radiation therethrough;
   b. a semiconductor substrate mounted within the detector housing, the substrate having three apertures therein;
   c. a dielectric membrane spanning each of the three apertures and formed on the bottom of the substrate;
   d. a first, a second and a third thermopile detector, the hot junctions of each thermopile detector being formed over one of the apertures on the dielectric membrane spanning the aperture, and the cold junctions of each thermopile detector formed over the substrate;
   e. a first interference bandpass filter mounted on the top side of the substrate so that the first filter covers the aperture above the first detector and the first filter is interposed between the port and the first detector, the first interference bandpass filter designed to pass incident radiation at a first spectral band;
   f. a second interference bandpass filter mounted on the top side of the substrate so that the second filter covers the aperture above the second detector and the second filter is interposed between the port and the second detector, the second interference bandpass filter designed to pass radiation at a second spectral band;
   g. a third interference bandpass filter mounted on the top side of the substrate so that the third filter covers the aperture above the third detector and the third filter is interposed between the port and the third detector, the third interference bandpass filter designed to pass radiation at a third spectral band; and h. leads extending through the detector housing and electrically connected to the first, second, and third thermopile detectors.

15. An infrared detector assembly according to claim 14, wherein the dielectric membrane is selected from the group consisting of silicon oxide, silicon nitride, and a multilayer structure of silicon oxide and silicon nitride.

16. An infrared detector assembly according to claim 14, further comprising a signal processor fabricated on the substrate, and wherein the first, second and third thermopile detectors are electrically connected to the signal processor and the leads are electrically connected to the signal processor.

17. An infrared detector assembly according to claim 14, wherein the first, second, and third interference bandpass filters are bonded to the substrate using a thermally conductive material.

18. An infrared detector assembly comprising:
   a. a detector housing having a port for receiving infrared radiation therethrough;
   b. a semiconductor substrate mounted within the detector housing, the substrate having three apertures therein and a raised rim on the top of the substrate surrounding each of the apertures;
   c. a dielectric membrane spanning each of the three apertures and formed on the bottom of the substrate;
   d. a first, a second and a third thin film thermopile detector, the hot junctions of each thermopile detector being formed over one of the apertures on the dielectric membrane spanning the aperture, and the cold junctions of each thermopile detector being formed over the substrate;
   e. a first interference bandpass filter mounted on top of the raised rim surrounding the aperture the first detector is formed over so that the first filter is interposed between the port and the first detector, the first interference bandpass filter designed to pass incident radiation at a first spectral band;
   f. a second interference bandpass filter mounted on top of the raised rim surrounding the aperture the second detector is formed over so that the second filter is interposed between the port and the second detector, the second interference bandpass filter designed to pass radiation at a second spectral band; and
   g. a third interference bandpass filter mounted on top of the raised rim surrounding the aperture the third detector is formed over so that the third filter is interposed between the port and the third detector, the third interference bandpass filter designed to pass radiation at a third spectral band.

19. An infrared detector assembly according to claim 18, further comprising an active infrared light source operatively mounted within the detector assembly.

20. An infrared detector assembly according to claim 19, wherein the dielectric membrane is selected from the group consisting of silicon oxide, silicon nitride, and a multilayer structure of silicon oxide and silicon nitride.

21. An infrared detector assembly according to claim 19, further comprising output leads extending through the detector housing and electrically connected to the first, second and third thermopile detectors.

22. An infrared detector assembly according to claim 19, further comprising:
   a. a signal processor fabricated on the substrate, the signal processor being electrically connected to the thermopile detectors; and
   b. leads extending through the detector housing and electrically connected to the signal processor.

23. An infrared detector assembly according to claim 19, wherein the first, second, and third interference bandpass filters are bonded to the substrate using a thermally conductive material.

24. An infrared detector assembly according to claim 19, wherein the active infrared light source comprises a tungsten filament.

25. A passive source infrared gas sensor, comprising:
   a. a detector housing having a port for receiving infrared radiation therethrough;
   b. a substrate mounted within the detector housing, the substrate having three apertures therein;
   c. a first, a second and a third thermopile detector fabricated on the bottom side of the substrate, the hot junctions of each thermopile detector positioned over one of the apertures in the substrate so as to receive radiation transmitted through the aperture, and the cold junctions of each thermopile detector positioned over the substrate;
   d. a first interference bandpass filter mounted on the top side of the substrate so that the first filter covers the aperture above the first detector and the first filter is interposed between the port and the first detector, the first interference bandpass filter designed to pass incident radiation at a first non-neutral spectral band which is absorbable by a preselected gas to be monitored;
   e. a second interference bandpass filter mounted on the top side of the substrate so that the second filter covers the aperture above the second detector and the second filter is interposed between the port and the second detector, the second interference bandpass filter designed to pass radiation at a first neutral spectral band;
   f. a third interference bandpass filter mounted on the top side of the substrate so that the third filter covers the aperture above the third detector and the third filter is interposed between the port and the third detector, the third interference bandpass filter designed to pass radiation at a second neutral spectral band; and
   g. signal processing circuitry connected to the electrical outputs produced by the first, second, and third detectors for producing a signal in response thereto representative of the concentration of the gas being measured.

26. A passive source infrared gas sensor according to claim 25, wherein the gas being monitored is at least one selected from the group consisting of CO, $CO_2$, $H_2O$, and TVOC.

27. A passive source infrared gas sensor according to claim 25, wherein the first, second, and third bandpass filters are about 0.1 μm wide at FWHM.

28. A passive source infrared gas sensor according to claim 27, wherein the second and third bandpass filters have a center wavelength selected from the group consisting of 3.91 μm, 5.00 μm, and 9.00 μm.

29. A passive source infrared gas sensor according to claim 28, wherein the first bandpass filter has a center wavelength selected from the group consisting of about 4.26 μm and about 4.67 μm.

30. An infrared gas sensor, comprising:
   a. a detector housing having a port for receiving infrared radiation therethrough;
   b. a substrate mounted within the detector housing, the substrate having three apertures therein;

c. a first, a second and a third thermopile detector fabricated on the bottom side of the substrate, the hot junctions of each thermopile detector positioned over one of the apertures in the substrate so as to receive radiation transmitted through the aperture, and the cold junctions of each thermopile detector positioned over the substrate;

d. a first interference bandpass filter mounted on the top side of the substrate so that the first filter covers the aperture above the first detector and the first filter is interposed between the port and the first detector, the first interference bandpass filter designed to pass incident radiation at a first spectral band;

e. a second interference bandpass filter mounted on the top side of the substrate so that the second filter covers the aperture above the second detector and the second filter is interposed between the port and the second detector, the second interference bandpass filter designed to pass radiation at a second spectral band;

f. a third interference bandpass filter mounted on the top side of the substrate so that the third filter covers the aperture above the third detector and the third filter is interposed between the port and tile third detector, the third interference bandpass filter designed to pass radiation at a third spectral band;

g. an active infrared light source operatively mounted within the detector assembly;

h. a source driver electrically connected to the active infrared source for driving the active infrared light source at a predetermined frequency; and i. signal processing circuitry connected to the electrical outputs produced by the first, second, and third detectors for producing a signal in response thereto representative of the concentration of at least one gas being monitored.

31. An infrared gas sensor according to claim 30, wherein the gas being monitored is at least one selected from the group consisting of CO, $CO_2$, $H_2O$, and TVOC.

32. An infrared gas sensor according to claim 30, wherein the first, second, and third bandpass filters are about 0.1μm wide at FWHM.

33. An infrared gas sensor according to claim 32, wherein the second and third bandpass filters have a center wavelength selected from the group consisting of 3.91μm, 5.00 μm, and 9.00 μm.

34. An infrared gas sensor according to claim 33, wherein the first bandpass filter has a center wavelength selected from the group consisting of about 4.26 μm and about 4.67 μm.

35. A passive source infrared gas sensor, comprising:

a passive infrared source comprising an infrared black surface;

b. a three channel infrared detector assembly centered in the passive infrared source, the detector assembly having a port for receiving infrared radiation therethrough; and c. a concave mirror facing the port of the detector assembly and the infrared black surface, the concave mirror being positioned such that radiation emitted from the passive infrared source is reflected from the mirror into the port.

36. A passive source infrared gas detector according to claim 35, wherein the infrared black surface comprises a material selected from the group consisting of black chrome oxide, bismuth oxide and carbon black.

37. A passive source infrared gas detector according to claim 35, wherein the passive infrared source comprises a concave infrared black surface.

38. A passive source infrared gas detector according to claim 35, wherein the three channel detector assembly comprises three infrared thermopile detectors and three interference bandpass filters, each filter being disposed in the optical path between the passive infrared source and one of the thermopile detectors.

* * * * *